United States Patent [19]

Forster et al.

[11] Patent Number: 4,598,162
[45] Date of Patent: Jul. 1, 1986

[54] DETERGENT RANGE ALDEHYDE AND ALCOHOL MIXTURES AND DERIVATIVES, AND PROCESS THEREFOR

[75] Inventors: Denis Forster, St. Louis; George F. Schaefer, Olivette; George E. Barker, St. Louis, all of Mo.

[73] Assignee: Monsanto Company, St. Louis, Mo.

[21] Appl. No.: 549,524

[22] Filed: Nov. 4, 1983

Related U.S. Application Data

[63] Continuation-in-part of Ser. No. 499,967, Jun. 1, 1983, abandoned, and a continuation-in-part of Ser. No. 272,587, Jun. 11, 1981, Pat. No. 4,426,542, which is a continuation-in-part of Ser. No. 256,439, Apr. 22, 1981, abandoned, which is a continuation of Ser. No. 104,517, Dec. 17, 1979, abandoned.

[51] Int. Cl.$^4$ .............................................. C07C 47/21
[52] U.S. Cl. .................................. 568/448; 568/451; 568/463; 568/840; 568/845; 568/850
[58] Field of Search ............... 568/451, 454, 840, 902, 568/909, 448, 842, 463, 845, 843, 850

[56] References Cited

U.S. PATENT DOCUMENTS

| | | | |
|---|---|---|---|
| 2,654,772 | 5/1950 | Pavlic | 568/840 |
| 2,793,236 | 5/1957 | Habeshaw et al. | 568/882 |
| 2,934,568 | 4/1960 | Barker | 260/615 |
| 3,119,876 | 1/1964 | Jaros et al. | 568/451 |
| 3,127,451 | 3/1964 | Berkeley, Jr. et al. | 568/882 |
| 3,401,206 | 9/1968 | Wulf et al. | 570/220 |
| 3,763,247 | 10/1973 | Lemke et al. | 568/882 |
| 3,821,311 | 6/1974 | Hughes et al. | 568/882 |
| 4,032,578 | 6/1977 | Savini | 568/463 |
| 4,183,871 | 1/1980 | Tavs et al. | 568/454 |
| 4,306,084 | 4/1981 | Petit | 568/454 |
| 4,426,542 | 1/1984 | Barker et al. | 568/883 |
| 4,438,286 | 3/1984 | Suzukamo et al. | 568/840 |
| 4,487,972 | 12/1984 | Haag et al. | 568/454 |

FOREIGN PATENT DOCUMENTS

| | | | |
|---|---|---|---|
| 0052999 | 11/1981 | European Pat. Off. | 568/882 |
| 881979 | 8/1961 | United Kingdom | 568/451 |

OTHER PUBLICATIONS

Crauland et al, Surfactant Congress, No. 4, vol. 1, p. 93 (1967).
The IFP Dimersol ® Process for the Dimerization of $C_3$ and $C_4$ Olefinic Cuts, Yves Chauvin et al.
Monick, "Alcohols: (1968), p. 475.
Wagner-Zook, Synthetic Organic Chemistry, (1965), pp. 149-152, 174-176.

Primary Examiner—Werren B. Lone
Attorney, Agent, or Firm—Joseph D. Kennedy; James W. Williams, Jr.

[57] ABSTRACT

Novel, liquid mixtures of isomeric aldehydes and alcohols are described in the $C_{11}$–$C_{16}$ carbon range, the compounds being characterized by a main carbon branched at the position and moderate additional branching in most isomers; the aldehyde mixtures are prepared by an economic route from olefins involving oxo and aldol reaction with the reaction conducted in such a way as to give a high percentage of aldolable product, and preferably with a base catalyzed aldol reaction conducted under conditions to make high conversions attainable. The aldehyde mixtures can be hydrogenated to alcohols and converted to novel ethoxylates or sulfate compositions suitable for use as biodegradable detergents; or hydrogenated and oxidized to novel carboxylic acid compositions also suitable for detergent use.

13 Claims, 2 Drawing Figures

DETERGENT RANGE ALDEHYDE AND ALCOHOL MIXTURES AND DERIVATIVES, AND PROCESS THEREFOR

This application is a continuation-in-part of application Ser. No. 499,967, filed June 1, 1983 now abandoned and of Ser. No. 272,587, filed June 11, 1981, now U.S. Pat. No. 4,426,542 which is a continuation-in-part of application Ser. No. 256,439, filed Apr. 22, 1981 as a continuation of Ser. No. 104,517, filed Dec. 17, 1979 both abandoned.

The present invention is concerned with a process for preparing detergent hydrophobes from olefin feedstock, and with novel detergent range aldehyde, alcohol and acid hydrophobes.

BACKGROUND OF THE INVENTION

The principal commercial surfactants in use today are linear alkylbenzene sulfonates and linear alcohol ethoxylates. The hydrophobic portion of both surfactants is a linear alkyl chain of between eleven and eighteen carbon atoms. These surfactants had been preceded by synthetic detergents which contained highly branched groups as a hydrophobic portion. The change to the currently employed linear groups, which occurred in the 1960's, was prompted by concern over the slow biodegradation characteristics of the branched hydrophobes. The perceived need for linearity led to development of particular approaches to hydrophobe preparation. The linear alkyl benzene sulfonates are based upon linear olefins derived from paraffins, which in turn are obtained through molecular sieve separations from paraffin mixtures. The linear alcohols based detergents are produced by way of ethylene oligomerization, followed by processes to manipulate the broad range of olefins obtained into the desired molecular weight range. The processing involved in such approaches adds considerably to energy and facilities usage and consequently to product cost. When olefins of the requisite carbon atom number have been obtained, they can be hydroformylated to produce aldehydes, generally with one more carbon atom than the olefin, which can be hydrogenated to an alcohol.

An alternate method for generating longer chain alcohols from short chain olefins is via a sequence involving hydroformylation (or oxo reaction) followed by aldol condensation and hydrogenation. Thus 2-ethylhexanol is prepared on a very large scale by (a) hydroformylating propylene to a mixture of n-butanal and isobutanal, (b) separating the mixtures of aldehydes (c) aldol reaction of n-butanal to 2-ethylhexenal and (d) hydrogenation of 2-ethylhexenal to 2-ethylhexanol. While this approach is well-recognized to be cost effective for generation of medium chain alcohols, it has not heretofore been shown to be an economical method for generation of longer chain alcohols. Among patents teaching conversion of aldehydes to higher aldehydes by the well known aldol reaction is U.S. Pat. No. 2,852,563.

Medium chain length olefins are usually derived from dimerization or oligomerization of ethylene or propylene. Among dimerization processes is the Dimersol ® dimerization process for dimerizing olefins using a nickel coordination complex and an aluminum alkyl as catalyst. The process can convert propylene to hexenes with selectivity in excess of 85%. The hexenes can be converted by oxo reaction to aldehydes and then alcohols, producing heptanols. Processes are also known for dimerizing propylene with trialkylalumminum metals to 4-methyl-1-pentene, see Industrial Organic Chemistry, Klaus Weissermel and Hans-Jurgen Arpe; English translation by Alexander Muller (Verlag Chemie, Weinheim, New York, 1978), pp 75–77. Also oxo reactions of certain branched olefins have been studied; see M. Johnson, . Chem Soc. 1963, 4859; Piacenti et al, J. Chem. Soc., 1966, 488; and Vysokinskii et al, J. Applied Chemistry of USSR, 1972, Vol. 45, pp. 1352–1355. Also oxo reactions of certain non-terminal octenes have been reported to give less than 60% of the straight chain aldehyde isomers, see Kummer et al, Homogeneous Catalysis-II, pages 19 to 26, Advances in Chemistry Series 132 (Edited by Denis Forster and James F. Roth), American Chemical Society, Washington D.C., 1974.

Reactions of the type described characteristically produce mixtures of products, often with extensive branching. Therefore, in order to control the branching, or to eliminate unreactive components, it has been common practice to employ distillation at intermediate stages to remove some of the isomers.

SUMMARY OF THE INVENTION

The invention is concerned with a process in which olefins selected from those with 3 to 7 carbon atoms are converted to aldehydes with 4 to 8 carbon atoms, which are then subjected to aldol condensation to obtain aldol products in relatively high yield. The aldehydes can be hydrogenated to alcohols having useful properties and derivative uses, with especial interest in conversion of hexenes to heptanals and to $C_{14}$ alcohols for use in detergents. The aldehydes can also be converted to other compounds useful as detergents or for other purposes. The invention is particularly concerned with the foregoing process in which the olefins have 5 to 7 carbon atoms and are converted to aldehydes with 6 to 8 carbon atoms, and then to enals and saturated aldehydes with 12 to 16 carbon atoms, in the detergent hydrophobe range. Such processes and the aldehyde, alcohol and detergent derivative products thereof are particularly exemplified herein by processes leading to, and products mainly composed of, compounds with 14 carbon atoms. The conditions of the exemplary process are generally applicable to those employing other reactants in the stated carbon atom ranges.

The present invention particularly concerns a hydrophobe aldehyde or alcohol mixture composed almost entirely of $C_{14}$ aldehydes or alcohols with a structure branched at the 2-position, with the alcohols being generally 2-pentylnonanols, i.e. having a five-carbon alkyl group substituted on the 2-position of a nine-carbon alkanol; with most of the isomers in the mixture having moderate additional branching, primarily methyl groups. The mixture is liquid at ambient temperatures and the hydrophobe groups of the alcohols are such as to make the mixture useful for formation of very effective detergents. The alcohol structures are further characterized by the absence of quaternary carbon or other structures strongly resistant to biodegradation, while generally having vicinal branching within limited ranges, and are still suitably biodegradable. The invention is further concerned with other aldehydes and alcohol mixtures of such 2-branched structure, but with 11 to 16 carbon atoms., e.g. ethyl-nonanol and hexyl-decanols.

The invention is further directed to processes for converting olefins to described C$_{14}$ aldehydes and alcohols, involving dimerization, oxo, aldol and hydrogenation processes based on propylene. In particular, a process involves conducting an oxo reaction with a hexene mixture comprised mainly of methyl pentenes, as produced by dimerization of propylene, and obtaining a heptanal product in which carbonylation has occurred primarily on terminal carbon so that upwards of 75% of the heptanal isomers are unbranched at the 2-position and capable of reacting directly in aldol reactions under basic conditions; and conducting an aldol reaction of the heptanal product to obtain C$_{14}$ aldehydes which are then hydrogenated to C$_{14}$ alcohols. The invention further includes use of cobalt catalyst in the oxo procedure under conditions to produce high percentages of desired aldolable product, and utilization of a co-solvent and suitable aldol conditions to obtain the C$_{14}$ product. Fortuitously, it has been found that in the hydroformylation of isomeric hexenes, the formylation of the prominent 2-methyl-2-pentene isomer occurs primarily on a terminal bond, with the percentage of such terminal formylation being much higher than that generally characteristic of hydroformylation of internal olefins; and a high percentage of aldolable product is obtained from terminal formylation of isomeric hexenes. The present invention involves an efficient process for converting propylene dimers to detergent hydrophobe alcohols in high overall yields such as 70% or better, and the alcohols are suitable for conversion to detergents having detergent and biodegradation properties comparable to those of the common commercial detergents. Moreover, the present process provides a much more efficient and economical route to detergent hydrophobes from olefin feedstock than that provided by the routes prominent in present commercial use. This route permits detergent alcohols to be built up from low cost propylene as compared to present commercial processes based on ethylene. In the processes of the invention, the immediate precursor of an alcohol is an aldehyde, and the aldehydes can also be converted to other useful compounds.

DETAILED DESCRIPTION OF THE INVENTION

Figure 1:
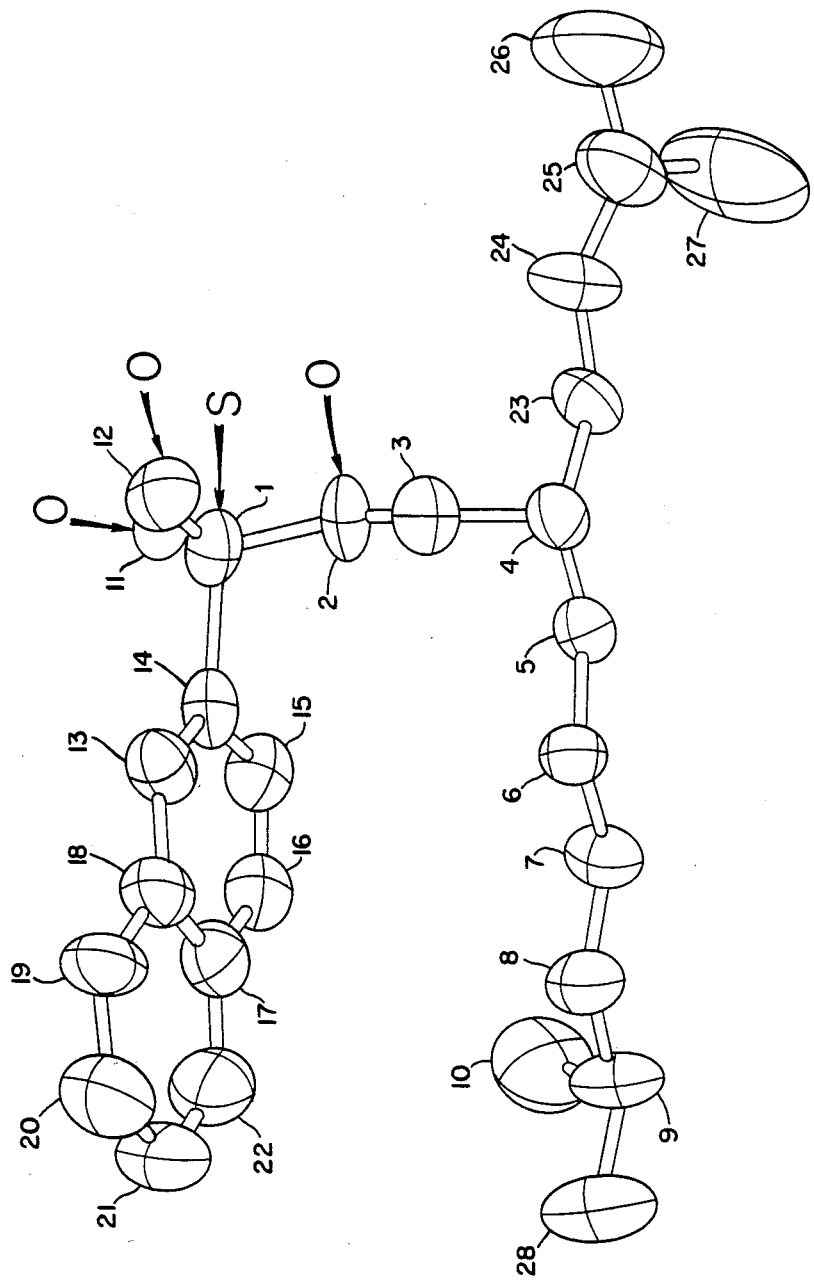

The C$_{14}$ alcohols of the present invention can be represented:

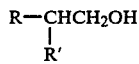

in which R is an alkyl group with seven carbon atoms and R' is an alkyl group with five carbon atoms. In a high percentage of the alcohols in the mixture, generally more than 80–85% or so, R' is selected from n-pentyl, 3-methylbutyl and 1-methylbutyl, and R is selected from n-heptyl, 3-methylhexyl, 5-methylhexyl, 2-methylhexyl and 2-ethylpentyl groups. While there will be some variance in the alcohol mixture with variation in preparation conditions, generally close to 50% or so of the alcohol mixture will be composed of 2-(3-methylbutyl)-5-methyl-octanol, 2-(1-methylbutyl) 5-methyloctanol and 2-pentyl-5-methyloctanol. Considering the type of branching involved, close to 50% or so by weight of the alcohols will have branching not only at the 2-position, but with each branch having an additional methyl branch, i.e. with R' and R in the above formula being selected from methylbutyl and methylhexyl groups respectively. The alcohols are also characterized as generally having a limited amount of vicinal substitution, i.e. substitution or branching on adjacent carbon atoms, and little or virtually no di-substituted carbon chain atoms, i.e. quaternary carbon atoms. Significant amounts of alcohols with quaternary carbon atoms have not been found in product analyses, and the types of reactants and reactions used in product preparations make it very unlikely that significant amounts of such alcohols would be found in unidentified portions of products. The lack of quaternary carbon in the alcohols of the mixture is fortunate in that such carbon is ordinarily resistant to biodegradation.

The described alcohols are obtained by hydrogenation of aldehydes of the same structure, and such aldehydes are similarly useful for their hydrophobe character and convertability to useful detergent or other derivatives. Such aldehydes are represented by the formula:

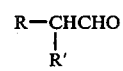

or when still in the enal form:

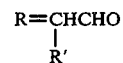

where the double bond is to one of the carbons of the R group. In such formulae, R and R' have the same meanings as described with respect to the alcohols, except that R in the enal is now alkylidine. For alcohols, enals and saturated aldehydes of twelve carbon atoms, R has six carbon atoms, and R' has four; and for sixteen carbon atoms R has eight carbon atoms and R' has six. R and R' will similarly vary for other structures having 11 to 16 carbon atoms, R from 6 to 8 carbon atoms, and R' from 2 to 6 carbon atoms. As with the C$_{14}$ alcohols, the C$_{11}$, C$_{12}$, and C$_{16}$ aldehydes and alcohols will often have branching not only at the 2-position, but with each branch having an additional methyl or ethyl branch.

A useful group of the unsaturated aldehydes of the present invention can also be represented:

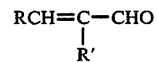

in which R plus R' total 8 to 13 carbon atoms and in which often in a high percentage (75%) of the unsaturated aldehyde, alkyl branches R and R' can be branched also with branching being limited to methyl or ethyl groups.

With further regard to the particular C$_{14}$ alcohol mixture, approximately 40 to 60% by weight will generally be the 2(3-methylbuty)-5-methyloctanol, 2-(1-methylbutyl)-5-methyloctanol and 2-pentyl-5-methyloctanol; and at least about 65% and possibly 65 to 80% or so by weight will be comprised of these alcohols, along with 2-(3-methylbutyl)-7-methyloctanol, 2-pentylnonanol,2-pentyl-7-methyloctanol and 2-(3-methylbuty)-nonanol. In addition to the indicated ranges of these alcohols, various other C$_{14}$ isomers will be present in small percentages, particularly those other alcohols listed in Table 4 herein, in amounts by weight usually approximating those in the Table and generally no more than 5% each and usually in ranges up to 1 to 2% or so, and with the balance of the $C_{14}$ alcohols being generally composed of the other alcohols in Table 3 herein, which will generally be present only in small percentages of each isomer. It will be noted that those isomers present only in small amount, with no amount reported in Table 4, but included in Table 3, tend to be more highly branched, i.e. multi-branched, than the other isomers, although most branches are still methyl, or occasionally ethyl groups. Taking these isomers into consideration, the amount of vicinal branched material may range as high as 20 to 35% or so by weight of the $C_{14}$ alcohols. However, the mixtures of alcohol isomers are biodegradable as indicated by tests reported herein. One of the alcohols which can be present in fairly good proportion, such as 10 to 20% or so, 2-(1-methyl-buty)-5-methyloctanal is a vicinal branched alcohol. The alcohols in the mixture are characterized by a fair degree of branching, although the alcohols present in large amount tend to be less branched than some of the minor components. Thus the 18 or so alcohols constituting about 90–95% or so by weight of the alcohols have an average of slightly more than 2 branches, about 2.2 to 2.4 branches, while the other 5 to 10% of the alcohols may have upwards of above 3.5 branches, such as 3.75–3.8 branches.

In addition to the novelty of the $C_{14}$ alcohol mixtures of the present invention, the particular alcohols are also new except for the 2-pentylnonanol. Thus the other 27 alcohols named in Table 3 are new compounds suitable for formation of nonionic detergents.

The alcohols comprising most of the present alcohol mixtures produced from branched hexenes can also be represented by the formula:

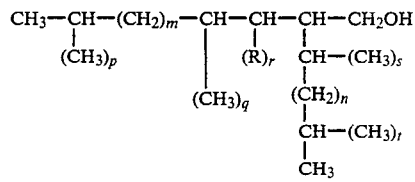

wherein:
R = methyl or ethyl;
p, q and r = 0 or 1; but only one of p, q and r can be 1;
m = 3, when p, q and r = 0;
m = 2, when p or q = 1;
m = 2, when r = 1 and R = methyl;
m = 1, when r = 1 and R = ethyl;
n = 2, when s and t = 0;
n = 1, when s or t = 1;
s and t = 0 or 1, but only one of s and t can be 1.

The alcohol mixtures, and the individual components thereof, are liquids at ambient temperatures. This is advantageous in that the alcohols can be more readily transferred from one vessel to another, or moved by pumping through conduits, etc., than is the case with solid alcohols. Also the liquid form is more convenient for mixing with reactants and solvents for conversion to detergent compounds or other useful products as contemplated. It happens that $C_{14}$ alcohols with straight chains, or with considerably less branching than the present alcohols, are generally solids. Thus detergent alcohols obtained by way of ethylene oligomerization, such as 75% to 80% normal primary $C_{12-15}$ alcohols and 75% normal $C_{14}$ primary alcohols, consisting of the designated percentages of normal alcohols and the balance of isomeric 2-alkyl(primarily 2-methyl)primary alcohols, are solid materials. Mixtures of aldehydes can also be represented by the above formula, with the $CH_2OH$ group replaced by $-CHO$. For the corresponding enal structure, there is unsaturation at the 2-position:

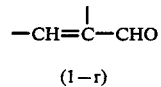

(1–r)

The detergent alcohols of the present invention are particularly suitable for conversion to nonionic detergents of good detersive and biodegradation properties. The largest volume use of detergent alcohols is as nonionic surfactants. The polyethoxylate surfactants are particularly important, and can be generated from the present alcohols by base catalyzed reaction between ethylene oxide and alcohol:

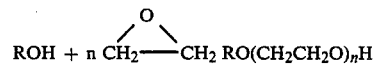

Typical values of n are in the range of 6 to 12, and R represents the alkyl portion of the alcohol, which for the present alcohols is generally a 14-carbon alkyl group. Ethoxylates prepared from the present alcohols were tested for detergency and found to be comparable to a leading commercial nonionic detergent under a variety of washing conditions. The commercial detergent is that prepared from $C_{12-15}$ alcohols of 75–80% linearity, Neodol ® 25.

In addition to detersive properties, another concern with surfactants has been biodegradability. The first major synthetic detergents were so-called alkylbenzene sulfonates, with an alkyl hydrophobe group derived from propylene tetramer. The propylene tetramer was produced by acid catalyzed polymerization and hence was highly branched, including extensive quaternary branching. This gave rise to a product with rather poor biodegradation properties, which led to extended life for surfactant properties in rivers and lakes. Public concern over the aesthetic impact (foam) and possible toxicity of long lasting surfactants led to a voluntary change over to predominatly linear hydrophobes. Prominent among current surfactants are linear alkylbenzene sulfonate and the linear alcohol ethoxylates discussed above. The linear alkylbenzene sulfonate (LAS) involves a linear alkyl group substituted on a benzene ring, generally at one of the secondary carbon atoms of the alkyl group. LAS has been found to be a suitably biodegradable detergent, although being degraded somewhat more slowly in standard tests than the substantially linear alcohol ethoxylates. The ethoxylates produced from the alcohols of the present invention are comparable in biodegradation to LAS, and therefore suitable in this regard. It is fortunate to find that the present alcohols are biodegradable, despite the presence of multiple branching. The substantially linear alcohol ethoxylates, such as Neodol ® 25, are known to be biodegradable, but those alcohols include substantial percentages of linear alcohols, and the branching is ordinarily only a single methyl or other lower alkyl group. In contrast, most of the alcohols in the present mixture have more than two alkyl branches. It is advantageous to be able to produce the present detergent alcohols, of properties comparable to Neodol ® alcohols, in a more efficient process and from a less expensive feedstock, i.e. from propylene rather than from ethylene.

The enals and aldehydes produced in the present process are also suitable for conversion to other useful compositions. Thus, in accord with the discovery of one of the present applicants, olefins can be converted to useful amine compounds by reactions involving hydroformylation and aldol reactions, followed by reaction with amines to obtain substituted amines. The reaction can be effected at the enal stage, or with the saturated aldehydes. Thus tetradec-2-enals or tetradecanals are reacted with a secondary amine under reductive conditions to obtain tetradecyl amines, e.g. dimethyl amine gives N,N-dimethyltetradecylamines. Use of a primary amine gives di(tetradecylamines), e.g. with mono-methyl amine, di-(tetradecyl)methylamines are produced. The amines with one or two long chain hydrophobe groups have detergent properties, and can be oxidized to amine oxides which also have detergent properties, or quaternized to ammonium salts which have interesting germicidal and other properties. Thus the present invention provides aldehydes which can be utilized for production of amines or ammonium compounds with useful properties. The aldehydes can also be converted to the corresponding saturated or unsaturated acids in accord with procedures described herein. While some branched-chain acids in the detergent range have an objectionable odor, the $C_{11}$ to $C_{16}$ derivatives of the aldehydes described herein are expected to have suitably low odor in view of the type of branching involved.

Hexenes, as produced by dimerization of propylene with transition metal catalysts, as in the Dimersol ® dimerization process, are characterized by being composed mainly of internal olefins, and a linear content which has a range from about 20% up to 32% or so. The main isomer present is a 2-methyl-2-pentene, along with other 2- and 4-methyl pentenes and around 6% 2,3-dimethyl-2-butene.

As indicated above, the linear content of propylene dimers is fairly low, being around 20% to 30% or so. At times there may be advantage in separating the linear components prior to conducting the present process. Separation can be effected by use of a molecular sieve or other suitable procedure. However, it has been found that the entire hexenes portion of the propylene dimerization product can be utilized as feedstock for the present oxo-aldol process. The branched isomers are typified by 2-methyl-2-pentene which, when subjected to oxo reaction with cobalt catalyst, has been found to be very selectively converted to 3-methyl and 5-methyl-hexanals. Fortunately it has been found that cobalt catalyst, in contrast to rhodium, has the effect of isomerizing the internal olefins so that the aldehyde group is predominantly on the end of the chain. It is very important to the use of propylene dimer in the present process, that, the oxo product is predominantly a non 2-branched alkanal., i.e. there is no substituent in the 2-position. Such aldehydes, which will directly react in base-catalyzed aldol reactions are sometimes referred to herein as "aldolable" aldehydes. As discussed herein, aldehydes with substituents in the 2-position do not readily undergo base-catalyzed aldol reactions. Thus if the internal hexenes were converted largely to such unreactive aldehydes, it would be very difficult to effect self-condensation of such aldehydes to a useful extent, and the use of propylene dimers in the present oxo-aldol process would be impractical. However, as discussed herein, the oxo process with cobalt catalyst converts the hexenes largely, e.g. 75 to 80% or so, to aldehydes which will react in the aldol reaction, making hexenes, obtained from propylene dimerization very suitable as a feedstock for producing detergent range alcohols in accord with the present invention. This result is surprising in view of the fact that oxo reactions of certain non-terminal octenes are reported to give less than 60% of straight chain aldehyde isomers. It appears that the methyl substitutent has some influence in directing the oxo reaction to obtain a great predominance of aldehydes with no substituent in the 2-position. There will similarly be advantage in using branched pentenes and heptenes in the present process, including those with no more than 20 to 30% linear content, even including those with mainly internal unsaturation, and obtain similarly good results in the oxo and aldol reactions taught herein.

Particular branched hexene isomers are converted to non 2-branched alkanals with very high selectivity, with 2-methyl-pentene-1 selectivity of better than 90% to such aldehydes being obtainable. The mixture of both branched and linear hexenes from propylene dimerization can be converted to such aldolable aldehydes with selectivity such as about 79% or so. In contrast, the selectivity to such aldehydes from the linear hexenes may be only 60% or so. Thus, surprisingly it is found that higher selectivity to aldehydes desirable for the aldol reaction can be obtained by using the crude hexenes mixture for the oxo reaction, rather than only the linear hexenes. Depending upon relative value and availability of the linear and branched hexenes, one might find advantage in using only the branched hexenes in the present process because of the high selectivity in the oxo process to aldehydes with no 2-branching suitable for aldol reaction.

The linear hexenes can be separated from the crude dimerization product by use of a molecular sieve or other suitable procedure, and the linear hexenes alone then subjected to an oxo reaction to obtain heptanal products, with the linear content of the heptanals ranging up to 75% or more. Branched isomers which may be present include 2-methylhexanal, and 2-ethylpentanal. The oxo product mixture can be reacted in an aldol reaction, employing aldol conditions as described herein, to produce aldol products. Under the aldol conditions employed, the n-heptanal reacts with itself at a rate about 10–15 times faster than it reacts with 2-methyl-hexanal or other 2-substituted aldehydes. Thus, when the $C_7$ aldehydes are produced from linear hexenes, a product compound predominantly of product from self-condensation of n-heptanal can be obtained by carrying out an aldol reaction of the oxo reaction product, with some control over the amount of product from 2-substituted aldehydes by controlling the amounts of conversion which is permitted. It may be desirable to have better than 50 to 60% completion for efficient use of feed stock, and conversion of 80% or higher may at times be desirable. The reaction can be run to achieve 95% or better conversion of the n-aldehyde to aldol product, while only about ¼ to ⅓ or so of the 2-substituted aldehydes are usually converted to aldol product by a cross-aldol reaction. With use of appropriate control, aldol product with about 80% to say 95% from self-condensation of n-heptanal can be obtained, for example at least 85% from self-condensation, with no more than 15% of cross-aldol product. Depending upon the properties desired in the product, the degree of branching can be controlled to a considerable extent by the present process. It happens that some known detergent range alcohols have a fair degree of branching and still have satisfactory biodegradability. Regardless of the desired degree of branching, there is advantage in being able to carry out an aldol reaction on the oxo product of the hexenes, without need for separating branched aldehyde isomers, and obtain a useful product, particularly considering the low cost nature of the feed stock and process. With a proper heptanal mixture, the process can be used to obtain a product composed of about 85% 2-pentylnonanol and 15% 2-pentyl-4-methyl-octanol.

The oxo process can generally be utilized to achieve 90-95% yields of aldehydes. With linear hexenes as reactant, selectivity to aldehydes without 2-substituents, i.e. α-aldehydealkanes, can be as high as 60 to 65%, but in large scale operation will possibly range from 50 to 65%.

The present invention employs an oxo reaction of substantially branched hexenes to obtain a mixture of aldehydes, which is then subjected to an aldol reaction. The oxo reaction involves contacting hexenes with hydrogen and carbon monoxide and hydroformylation catalyst under hydroformylation conditions suited to obtaining a high proportion of terminal formylation of the olefin feed. It is desirable to have the resulting aldehyde constitute 75 to 80% or more of the aldehyde product.

It is important that the hydroformylation of the mixed hexenes give a relatively high ratio of aldehydes without 2-branching, as this contributes to the feasibility of using the aldehyde mixture for an aldol reaction to obtain a good yield of aldol product. The use of moderate temperatures in the hydroformylation contributes to forming aldehydes without 2-branching, but reaction rate improves with temperature. Thus temperatures sufficient to produce an appreciable reaction rate, ranging from 80° to 100° C. or so can be used, and temperatures on up to 125°-140° C. can be employed to obtain better reaction rates. Still higher temperatures up to 150° C. or higher can be used. To some extent high catalyst concentrations can be employed to obtain reaction rates, even at relatively low temperatures. Cobalt catalyst is especially suited to obtain the desired high proportion of aldehyde with no 2-branches. Unmodified cobalt carbonyl catalyst can conveniently be used. Such catalyst conventionally designated as dicobalt octacarbonyl, can be provided or employed in many forms known to be useful as a hydroformylation catalyst, although it may be necessary to exercise some choice to provide catalyst best suited to obtaining a high proportion of aldehyde with product suitable for direct base-catalyzed aldol reaction. The above-referred to Ser. No. 272,587 disclosed conditions as above for hydroformylation of mixed linear butenes, stating that moderate temperatures in the hydroformylation contribute to obtaining about a 3:1 mixture of normal to branched aldehydes. The conditions can be used for hydroformylation of olefins with 3 to 7, or more narrowly, 5 to 7 carbon atoms. The Ser. No. 272,587 application further described as exemplary a process in which mixed butenes are converted to a ten-carbon plasticizer alcohol comprised of at least about 80-90% 2-propylheptanol by an oxo reaction of the butenes to obtain amyl aldehydes with at least about 66% n-pentaldehyde content, followed by an aldol reaction of the aldehydes under conditions to cause substantially all of the n-pentaldehyde to react but with incomplete conversion of branched aldehydes, and then hydrogenating to produce alcohols in which the ten-carbon alcohols are comprised of at least 80-90% 2-propylheptanol. Under the aldol conditions employed the 2-methylbutanal present does not readily condense with itself, and condenses at a comparatively slow rate with the n-pentanal, so that the 2-propyl-4-methylhexanol content (resulting from the so-called cross aldol of n-pentanal with 2-methyl-butanal) in the resulting alcohol is held to no more than about 15-20%, often 12% or less. Under the aldol conditions employed, the n-pentanal reacts with itself to form aldol product at a rate about 15 times greater than it reacts with 2-methylbutanal. The aldol reaction is permitted to go to 80% or so completion so that if about 25% of the aldehyde supplied is 2-methylbutanal, about $\frac{1}{3}$ of it will remain unreacted, and about 88% of the aldol product will be that from self-condensation of n-pentanal. The conversion of n-pentanal to aldol product will be very high and desirably nearly complete, such as upwards of 90 or 95%. There will be some variation with conditions and isomer content of the aldehydes utilized, but it was contemplated to obtain aldol product with about 80% to about 95% being from the self-condensation of n-pentanal, and preferably at least 85% from self-condensation with no more than 15% of 2-propyl-4-methylhexanal being produced. In the process, the aldol intermediate, 2-propyl-3-hydroxyl-heptanal, will ordinarily be dehydrated in the aldol procedure to 2-propylheptenal. Under some conditions the immediate aldol product can be isolated, but ordinarily under the temperature conditions employed the 2-propyl-2-heptenal is produced. In such procedure, it was desirable to have the n-pentanal to branched aldehyde ratio at least about 2.0:1, representing at least about 66.7% n-pentanal content. Aldehydes with 70-75% normal content, or even higher normal contents are desirable to the extent available from oxo reactions, possibly up to 85%, and will be useful for the aldol stage.

The oxo stage of the reaction can be conducted under the usual conditions pertaining to cobalt catalyzed hydroformylation reactions with attention to the temperature conditions as described above. Usual pressure conditions apply, such as 500–4000 or up to 5000 psi (3447.5–27,580 on up to 34,475 kilopascals) total pressure, with most of the pressure being from the carbon monoxide and hydrogen supplied. The carbon monoxide and hydrogen are conveniently used in 1:1 ratio and obtained from usual synthesis gas sources, but other ratios can be employed in keeping with known hydroformylation practice. The reaction can be carried to the desired stage of completion in 1 to 3 hours or so on a batch basis, temperature, pressure and catalyst concentration.

The reaction can be conveniently conducted either without a solvent or with solvents and, employing concentrations customary for homogeneous catalyst reactions, such as 2 to 10 molar or greater concentrations of the hexenes (or butenes or other olefins) in a solvent, e.g. hydrocarbon solvents such as toluene, and 0.1% to 1% by weight, based on cobalt, of catalyst.

The present invention is particularly concerned with preparing detergent range alcohols and aldehydes from propylene feedstock. The detergent range alcohols are somewhat higher in carbon number than plasticizer alcohols, often having 14 carbon atoms, but in some cases ranging from about 11 to about 16 or so carbon atoms. Propylene can be dimerized to hexenes, and the hexenes can be converted to aldehydes by an oxo reaction as described herein, and the resulting heptaldehydes can be reacted in an aldol reaction to produce aldol products which can be hydrogenated to $C_{14}$ alcohols. Using oxo product in which the content of aldehyde without 2-substitution may range from 60 up to near 80% or so, aldol conversions may approach 75 to 90%, even though participation of the 2-substituted aldehydes is limited, so that it is involved in cross-aldol producing no more than 20% of the product.

The aldol reaction is carried out for the most part utilizing the usual aldol catalysts and temperature conditions, using elevated temperatures upwards of 60° C., particularly temperatures of about 90° C. to 130° C., or possibly up to 150° C. or higher if desired, the conditions also being those disclosed for n-pentanal in Ser. No. 272,587. The reaction is operable over broad pressure ranges including pressures less than atmospheric as well as elevated pressures, but will usually be effected at slightly elevated pressures sufficient to maintain the reactants substantially in the liquid state. The reaction can also conveniently be conducted at reflux.

The aldol reaction can utilize strongly alkaline catalyst, such as sodium and potassium hydroxide, or sodium and potassium cyanide. The concentration of the aqueous alkali can be varied, but molar or similar concentrations of alkali metal hydroxides can be used, and concentrations selected will generally be in the range of about 1 to 10% by weight. The amount of aqueous alkali to aldehyde reactant can also vary, for example from about 15% by volume aqueous alkali up to about 75% by volume aqueous alkali. The aldol reaction will be run for a sufficient time to obtain the desired degree of conversion, which for batch reactions may be in the range of about 1 to about 3 hours, while in continuous reaction times of less than five minutes are achievable. The reaction is stopped by permitting the reaction mixture to cool and separating the organic reaction phase from the aqueous alkali phase.

In one major respect it is difficult to conduct aldol reactions of heptanals in conventional manner, as in aqueous NaOH, because this procedure requires appreciable solubility of the organic aldehyde in the aqueous phase, or vice versa. The mutual solubility is so low with $C_7$ aldehydes that little reaction occurs in reasonable time periods. However, it has been found that use of a co-solvent overcomes this problem and results in suitable reaction rates. In principle, any solvent with miscibility with both the aldehyde and the aqueous base, or at least some solubility with respect to each, will act to increase the rate of the reaction. It is also desirable that the solvent be relatively inert under the reaction conditions so as not to cause interfering reactions or to be readily degraded excessively by the hot basic medium. In general, polar solvents will tend to have the requisite solubility characteristics, and hydroxy alkanes, for example, alkane diols, having the appropriate solubility characteristics can be used. Hexanediol is very suitable. Methanol is also a suitable co-solvent.

In the aldol reactions involved in the present invention it is necessary to utilize a high proportion of aldehydes without 2-branching, also referred to herein as aldolable aldehydes, in order to achieve good yields of aldol. The 2-substituted aldehydes do not undergo self-condensation aldol reactions with any facility under the usual basic aldol conditions, although they will serve as acceptor molecules to some extent in cross-aldol reactions, as illustrated with the following heptanal isomers:

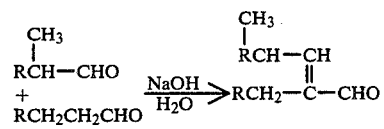

in which R represents a butyl group. However, the 2-substituted aldehydes react more slowly than other aldehydes, and therefore would constitute an undesirably high residue of unreacted component if provided to the reaction mixture in high proportion. In the present process with 75 to 80% or so of aldehydes without 2-branching, the aldol reaction can be conducted to include some cross-aldol of 2-substituted aldehydes so as to have yields of 85% or more based on starting aldehyde. In general, the $C_{14}$ aldehydes resulting from such cross-aldol reactions, and the alcohols produced therefrom, have properties comparable to those produced from aldol reactions of aldehydes without 2-substitution, and are suitably present in alcohol mixtures for detergent preparations as described herein. The conversion of aldehydes without 2-branching in such aldol reactions can be in the range of 95% or better while possibly only about $\frac{1}{4}$ to $\frac{1}{3}$ of the 2-substituted aldehydes are converted to aldol product.

The hydrogenation of the enals from the aldol reaction can be conducted under the usual catalytic hydrogenation conditions for reducing olefinic bonds and aldehyde groups. The carbon-to-carbon bond reduces more rapidly and at a lower temperature than the aldehyde group, e.g. at about 90° C., with cobalt on Kieselguhr catalyst at elevated hydrogen pressure. The hydrogenation will generally be carried out at 100–20000 psi, or greater hydrogen pressures and temperatures of 100° to 200° C. or higher, although any temperatures which are effective with a particular catalyst can be used. The stated conditions will be effective for reducing both the carbon-to-carbon bond and the aldehyde group to obtain saturated alcohol. Various other hydrogenation catalysts can be used including platinum and platinum on carbon catalysts, copper chromite, activated nickel, etc., and individual catalysts can be utilized in conjunction with other catalysts.

The present invention can include an oxo reaction, followed by an aldol reaction, and then a hydrogenation to convert enals to alcohols. For large scale operations, the oxo reaction will be conducted with usual provisions for separating gaseous reactants and products, and catalysts, from the aldehyde products, with recycle as appropriate. The aldehyde product mixture will then be subjected to an aldol reaction, followed by decantation and water washing or other simple procedures to separate the organic product-containing phase from the aqueous phase. The product phase is then hydrogenated, converting both unreacted heptanals and $C_{14}$ enals to the corresponding alcohols when the product phase is from a heptanal reaction. The hydrogenation is followed by a distillation to remove light ends, followed by a distillation to remove $C_7$ alcohols. Both the $C_7$ and $C_{14}$ alcohols can then be treated in further hydrogenation polishing operations to improve the alcohol quality by insuring complete hydrogenation.

The separation of the $C_7$ from $C_{14}$ alcohols is readily effected by distillation in equipment constructed of inexpensive alloys such as carbon steel. Separation at this stage is simple, compared to the difficult separation which would be required to separate the seven carbon aldehyde isomers prior to the aldol reaction.

As an alternate to the above procedure, it is possible to separate the unreacted seven-carbon aldehydes by distillation from the 14 carbon enals prior to hydrogenation. For convenience of separation, distillation of the alcohols is generally preferred, However, if the aldehydes are desired for some purpose, separation is appropriate, and this has the advantage of avoiding unnecessary hydrogen use. The aldehyde separation can, of course, be effected with other aldehydes, e.g. to separate five-carbon aldehydes from 10-carbon enals.

In the present process the oxo product is used in the aldol reaction without any need for separation of some of the components. This contrasts with the usual commercial procedure, for example, for preparing 2-ethylhexanol as a plasticizer alcohol, wherein it is the practice to remove isobutanal before conducting an aldol reaction with n-butanal. The separation is effected by distillation and, since isomeric aldehydes have similar boiling points, separation on a commercial scale involves high capital cost equipment with consequent expense, and a substantial energy cost. There is a definite advantage in avoiding such a distillation step in the present process.

The $C_7$ branched aldehydes which do not react in the aldol reaction can be separated from the reaction mixture for various purposes, or hydrogenated with the mixture and utilized as a $C_7$ branched alcohol. If desired, the branched $C_7$ alcohol can be dehydrated, and then subjected to an oxo reaction to produce an aldehyde with an additional carbon atom. Thus 2-methylhexanol can be converted to 2-methylhexene-1, which can be recycled to the oxo stage of the reaction process and hydroformylated to predominantly 3-methyl-heptanal. This 3-methylheptanal, not having any substituent in the 2-position, reacts at a good rate in the aldol reaction. Other unreacted aldehydes, such as 2,4-dimethylpentanal and 2-ethyl-pentanal, can similarly be hydrogenated and dehydrated and recycled to be converted in the oxo stage to $C_8$ aldehydes with no substituent in the 2-position, which will take part in the aldol reaction when recycled through that stage. This procedure to use the unreacted $C_7$ aldehyde results in greater conversion of the original reactants to the desired final product, rather than to a concomitant product such as $C_7$ alcohols. Use of this recycle feature in the oxo-aldol process changes the components of the product from mixed hexenes to some extent, but the properties will be similar as the main difference in the additional components will be an additional methyl substituent as in 2(1-methylbuty)-5-methylnonanol, 2-(3-methylbuty)-5-methylnonanol and 2-pentyl-5-methylnonanol, for example.

The Dimersol ® dimerization process has been referred to in various publications, e.g. see "How First Dimersol is Working" by Benedek et al, Hydrocarbon Processing, May 1980, page 143; also Chauvin et al, "The IFP Dimersol ® Process for the Dimerization of $C_3$ and $C_4$ Olefinic Cuts", Advances in Petrochemical Technology, presented at American Institute of Chemical Engineers, Apr. 13, 1976, Kansas City, Mo.

The combination of the Dimersol ® dimerization process, oxo process, aldol and hydrogenation provides a very efficient route from propylene to detergent range alcohols. One of the known routes to such alcohols relies upon oligomerization of ethylene to obtain higher molecular weight materials which are then subjected to an oxo reaction. The presently proposed route is in many respects more efficient and economical than those involving ethylene oligomerization, as propylene costs less than ethylene, and the reactions involved using dimerization, oxo and aldol are more straight forward than an oligomerization which can produce a broad mixture of products and require extensive equipment and procedures to direct it to suitable product. As discussed hereinabove, the mixture of isomers obtained from a dimerization can be carried through the oxo, aldol and hydrogenation reactions to obtain high overall conversions and yields, despite the presence of extensive branching in the materials. It is fortunate to find that a high proportion of the materials are capable of taking part sequentially in all of the required reactions, and in particular that the aldehyde failing to react to a significant degree in the aldol reaction, because of 2-substitution, is at a comparatively low level.

In the oxo stage of the present process it will be noted that cobalt catalyst is employed with the hexenes in order to promote migration of the olefinic bond and high selectivity to desired aldehyde isomers, such catalysts being for example $Co_2(CO)_8$ which may be equivalent to $HCo(CO)_4$ under reaction conditions.

The processes of the present invention can utilize mixtures with olefins of different carbon numbers, along with isomeric mixtures of olefins of particular carbon number. The oxo product of such mixtures can be subjected to aldol reactions as taught herein to give aldol product. Such procedures can, for example, use butenes in conjunction with Dimate ® hexenes. Also, Dimate ® hexenes may at times have various amounts of $C_5$, $C_7$ and $C_9$ olefins, and still be usefully employed in the present invention. Such processes will still have the advantage of production of high amounts of aldolable aldehydes in the oxo process, and result in aldol product with carbon numbers in the detergent range and with branched structure suitable for detergent use. Also, in the Dimersol ® process, butene can also be dimerized or codimerized with propylene, and this provides additional ways to modify the present process by variation of the olefin feed stock, while still producing aldol product in the detergent range. In the procedures which use mixed olefins, it is also possible to conduct the oxo reaction with olefins of different carbon number, and to combine the resulting oxo products for an aldol reaction. Another olefin of particular interest for use in the present process is 4-methyl-1-pentene, which can be produced by Na catalyst dimerization of propylene, as reported in Industrial Organic Chemistry, cited hereinabove. The reaction is conducted at approximately 150° C. and 40 bar, using $Na/K_2CO_3$. The 4-methyl-1-pentene in an oxo process will give very high aldolable product as shown by the results for 4-methyl-pentene-2 in Example 4, and is therefore well suited for use in the present process to prepare $C_{14}$ enals and detergent derivatives thereof.

The $C_{14}$ or other detergent range alcohols produced by the present process can be readily converted to detergents by known procedures. Thus non-ionic detergents are prepared by reaction with ethylene oxide to have a desired number of ethoxyl groups, e.g. 6 to 10 or 12 or so. These, or other ethoxylated alcohols, possibly with 2 to 3 ethoxyl groups can be reacted to form an alcohol ether sulfate, having a sulfate anionic end group with a sodium or other cation. The alcohols can also be reacted to prepared sulfate derivatives. The detergents thus prepared will have the requisite hydrophobic groups for detergent properties. Moreover, the structures are such as to provide biodegradability, in that the structures are acyclic alkyl groups which are essentially free of any quaternary carbon groups. There is some branching on adjacent carbon atoms, but that and the common 2-branching characteristic of aldol product, with or without various additional methyl or other lower alkyl branches in non-adjacent positions, do not have any important effect on the biodegradable nature of the compounds. An alcohol ether sulfate prepared from 2-pentylnonanol has been described as biodegradable by Crawland et al, Surfactant Congress No. 4, Vol. 1, page 93 (1967). Also Kravetz et al, Proceedings of the American Oil Chemists' Society, 69th annual meeting, May, 1978, St. Louis, MO., concluded that variation of branching from 45% to 75% linear had no appreciable effect on biodegradation rates of primary alcohol ethoxylates, and make reference to 58% branching giving biodegradation at rates not appreciably different from zero branching. The branching involved in both of these prior studies was a single branch, and this can be contrasted with the materials described herein which contain at least two branches in almost all cases.

A quantity of Dimate ® hexenes from a refinery stream was distilled to have a $C_6$ cut, approximately 73% of the total material. Analysis is given in Table 1. The Dimate ® hexenes had been produced by dimerization of propylene over a catalyst by the Dimersol ® process.

TABLE 1

Dimersol ® Hexene Distribution

| | % (100% basis) | |
|---|---|---|
| 2,3-dimethyl-2-butene | 4.5 | |
| 2-methyl-2-pentene | 35.6 | |
| trans-4-methyl-2-pentene | 18.4 | |
| cis-4-methyl-2-pentene | 3.7 | |
| 2-methyl-1-pentene | 5.1 | |
| 2,3-dimethyl-1-butene + 4-methyl-pentene-1 | 1.7 | |
| trans-2-hexene | 17.8 | |
| trans-3-hexene | 6.3 | 31.0% linear |
| cis-3 + cis-2 hexene | 6.8 | |
| 1-hexene | 0.1 | |

The distillation serves to remove some $C_5$, $C_7$ and $C_9$ hydrocarbons resulting from oligomerization involving some ethylene present in the original olefin feed, or trimerizations. It also removes $C_6$ chlorides, along with the $C_9$ hydrocarbons; these chlorides, resulting from the dimerization catalyst, could contaminate the oxo catalyst if not removed.

It is fortunate that the hexenes mixture is amenable to reaction at a good rate in the oxo reaction. It is sufficiently reactive to permit use of moderate conditions and equipment therefor, with suitable reaction rates and times. This is in contrast to an octenes Dimate ® mixture which is characterized by more relatively unreactive dibranched olefin isomers and much slower reaction rates. Such material requires more severe reaction conditions in more expensive equipment, and additional reactor capacity.

Since the oxo product is to be reacted in an aldol reaction, it is to be conducted under conditions which favor production of aldehydes as contrasted with alcohol or other products.

EXAMPLE 1

Hydroformylation of a Dimate hexenes mixture, of composition reported in Table 1, was carried out in an autoclave with agitation. The autoclave was charged with 0.52 g dicobalt octacarbonyl, 74.06 Dimate hexenes and 3000 psi. gauge (20,786 KPa) of 1:1 CO and $H_2$. The autoclave was heated to 130° C. and held for four hours. Liquid samples were taken every hour. The autoclave was cooled rapidly and the product removed under nitrogen. Analysis indicated 92% conversion of the olefins. The product was analyzed chromatographically, with results as reported in Table 2 (along with other examples). It will be noted that 77.9% of the aldehyde product was unbranched at the 2-position and therefore aldolable. This result was obtained, even though the hexene reactants were more than 90% composed of internal olefins, including some linear hexenes which give product little more than 50% aldolable. A similar run employing a 110° C. temperature with cobalt catalyst for 23 hours is also reported.

EXAMPLE 2

The autoclave of Example 1 was charged with 0.49 g. of dicobalt octacarbonyl, 69.84 g. 2-methylpentene-2 and 3000 psi gauge (20,786 KPa) of CO and $H_2$ in 1 to 1 ratio. The autoclave was heated to 130° C. and held at this temperature for three hours. The autoclave was cooled and the product removed under a blanket of argon, and analyzed. Conversion of the olefin was 83%. The procedure was repeated substantially, but employing a temperature of 116° C. for a 48% conversion. Results of the analysis are reported in Table 2. It is notable that better than 90% of aldehydes unbranched at the 2-position, i.e. aldolable aldehydes, were obtained. Approximately the same results were shown from samples taken during the reactions, with the 116° reaction at 1 hour giving 17% conversion and 35.4% 5-methylhexanal and 55.5% 3-methylhexanal; and the 130° reaction temperature 45% conversion at 1 hour with 32.5% 5-methylhexanal and 57.6% 3-methylhexanal.

EXAMPLE 3

Hydroformylation was carried out on 2-methyl-1-pentene with cobalt catalyst in accord with the procedure of Example 2 at 116° C. for a three-hour period. A 41% conversion was obtained, with 95% of aldolable aldehyde unbranched at the 2-position being obtained. Results are reported in Table 2.

EXAMPLE 4

Hydroformylation was effected with 4-methyl-2-pentene in accord with the Example 2 procedure, employing a 130° C. temperature. Results are reported in Table 2.

TABLE 2

| Example | Hexene | Temp. (°C.) | Run Time (hours) | Oxo Product Distribution % | | | | | | | | | % Aldolable* |
| --- | --- | --- | --- | --- | --- | --- | --- | --- | --- | --- | --- | --- | --- |
| | | | | I | II | III | IV | V | VI | VII | VIII | IX | |
| 1 | D-Mixture | 110 | 23 | 15.3 | 19.4 | 8.7 | 39.1 | 4.4 | 3.1 | 1.4 | 7.5 | 1.0 | 76.9 |
| " | D-Mixture | 130 | 4 | 14.9 | 25.0 | 8.5 | 36.2 | 4.3 | 1.8 | 1.1 | 7.4 | 0.8 | 77.9 |
| " | " | | 3 | 15.4 | 23.5 | 8.8 | 37.9 | 4.5 | 0.7 | 1.1 | 7.5 | 0.7 | 77.5 |
| " | " | | 2 | 16.8 | 25.5 | 9.6 | 33.8 | 4.9 | 0.8 | 1.0 | 7.2 | 0.6 | 76.9 |
| " | " | | 1 | 18.8 | 24.5 | 10.7 | 31.8 | 5.4 | trace | 1.4 | 6.8 | 0.5 | 75.1 |
| 2 | 2-methyl-2-pentene | 116 | 3 | — | 34.3 | — | 56.6 | — | — | 1.3 | 6.9 | 0.9 | 90.9 |
| " | 2-methyl-2-pentene | 130 | 3 | — | 33.6 | — | 56.6 | — | — | 1.4 | 7.2 | 1.2 | 90.2 |
| 3 | 2-methyl-1-pentene | 116 | 3 | — | 10.6 | — | 84.4 | — | — | 0.4 | 2.5 | 2.1 | 95.0 |
| 4 | 4-methyl-2-pentene | 130 | 3 | | 65.9 | | 17.3 | | trace | 1.6 | 15.3 | trace | 83.2 |
| | | | 2 | | 65.1 | | 16.6 | | | 1.6 | 16.8 | trace | 81.7 |
| | | | 1 | | 67.6 | | 14.2 | | | 1.4 | 16.8 | trace | 81.8 |

I = heptanal
II = 5-methylhexanal
III = 2-methylhexanal
IV = 3-methylhexanal
V = 2-ethylpentanal
VI = 3,4-dimethylpentanal
VII = 2,-ethyl-3-methylbutanal
VIII = 2,4-dimethylpentanal
IX = 2,2-dimethylpentanal

EXAMPLE 5

Hydroformylation was effected with 2,3-dimethyl-2-butene at 130° C., employing the procedure of Example 2. At 1, 2 and 3 hours conversions were respectively 18, 43 and 71%, and in each case the aldehyde product wss analyzed as 100% 3,4-dimethylpentanal, an aldolable aldehyde.

EXAMPLE 6

This example was a simulation of two oxo reactors operating at different temperatures. The autoclave was charged with 0.44 g. dicobalt octacarbonyl, and 73.94 g. Dimate hexenes. The autoclave was sealed, pressure checked and run under 3000 psig (20,786 KPa) of 1/1 CO to $H_2$ at 130° C. for 1 hour then heated to 140° C. for an additional 4 hours. The autoclave and contents were rapidly cooled and the product removed under nitrogen. Analysis of the final product yielded that the olefin was 97% converted with 83% as the aldehydes, 11% as alcohols, and 3% high boilers. The unreacted olefin consists of 2-methylpentene-2, 2,3-dimethylbutene-2 and trans-hexene-2. The aldehydes after normalization are 39% 3-methylhexanal, 20% 5-methylhexanal, 16% heptanal, 9% 2-methylhexanal, 6% 2,4-dimethylpentanal, 5%, 2-ethylpentanal, 4% 3,4-dimethylpentanal, 1% 2-ethyl-3-methylbutanal, 1% 2,2-dimethylpentanal. The aldehydes were distilled from the catalyst, unreacted starting material and other products at 20 mmHg from 41° to 45° C.

The percentage of aldehydes unbranched at the 2-position produced was 79%.

The results in Example 6 indicate that the percentage of aldehydes unbranched at the 2-position from branched hexenes (69% of hexenes) was 88.7%, compared to only 53.3% of such aldehydes from the linear hexenes (31% of hexenes). Considering only the methylpentenes (62.8%, ignoring the small amount with 2,4-dimethylbutene in Table 1), the aldolable aldehyde unbranched at the 2-position content of the aldehyde product was 86.6%).

EXAMPLE 7

An aldehyde mixture representative of that from the oxo reaction of Dimate ® hexenes, as described in Example 16, was reacted in an aldol reaction. An autoclave was charged with 50 ml of 0.8 M NaOH, 100 ml of 2,5-hexanediol under 20 psi gauge argon. Then 36.2 g., 50 ml, of the aldehydes were pressured into the autoclave with argon after the autoclave had been heated to 100° C. and agitation set at 1500 rpm. The reaction was run for an additional hour and the system rapidly cooled. The product was removed and the upper and lower phases were separated. The upper phase contained 16.8% unreacted aldehydes, 2.4% heptanols, 72.9% tetradecenals and 4.1% 2,5-hexanediol. The conversion of the aldehydes approximated 79%.

EXAMPLE 8

Unsaturated aldehydes representative of product from oxo and aldol reactions of Dimate ® hexenes as produced in Example 7, were subjected to hydrogenation. An autoclave was charged with 130.95 g of 45%+5% cobalt on Kieselguhr, 1336.1 grams of the aldol condensation product and hydrogen to 1500 psi gauge (10,644 KPa). The autoclave was carefully heated to 160° C., with gas uptake starting at 100° C. The pressure and temperature were maintained for 4½ hours. The catalyst was filtered off and washed with methanol to remove any residual alcohols. The material was then distilled using a 30 cm. vigreux column at 5 mm Hg. The $C_{14}$ alcohols were collected from 119° to 122° C. From analysis of the aldehydes prior to the aldol reaction, and analysis of derivatives of some of the alcohol components, together with gas chromatographic and other identification as included and described hereinbelow, it was concluded that the product includes some 28 alcohols in amounts and as named and illustrated by skeletal structure in Table 3 where the hydroxyl-bearing group is designated by an asterisk.

TABLE 3

Tetradecanols

| Structure | Name | Weight % |
|---|---|---|
| <pre>C C C C C C C C C C<br>    C     C*    C</pre> | 2-(3-methylbutyl)-5-methyloctanol | 25.4 |
| <pre>            C<br>C C C C C C C C C C<br>    C     C*</pre> | 2-(1-methylbutyl)-5-methyloctanol | 14.8 |
| <pre>C C C C C C C C C C C<br>    C           C*</pre> | 2-pentyl-5-methyloctanol | 13.4 |
| <pre>C C C C C C C C C C C<br>    C     C*    C</pre> | 2-(3-methylbutyl)7-methyloctanol | 7.0 |
| <pre>C C C C C C C C C C C C<br>              C*</pre> | 2-pentylnonanol | 6.0 |
| <pre>        C<br>C C C C C C C C C C<br>    C     C*    C</pre> | 2-(3-methylbutyl)-5,6-dimethylheptanol + | |
| <pre>            C   C<br>C C C C C C C C C C<br>          C*</pre> | 2-(1-methylbutyl)5,6-dimethylheptanol | 5.1 |
| <pre>C C C C C C C C C C C<br>    C           C*</pre> | 2-pentyl-7-methyloctanol | 4.1 |
| <pre>C C C C C C C C C C C C C<br>              C*    C</pre> | 2-(3-methylbutyl)-nonanol | 4.1 |
| <pre>            C<br>C C C C C C C C C C<br>    C     C*</pre> | 2-(1-methylbutyl)-7-methyloctanol | 2.4 |
| <pre>C C C C C C C C C C C<br>      C     C*</pre> | 2-pentyl-4-methyloctanol | 2.4 |
| <pre>C C C C C C C C C C C<br>    C           C*</pre> | 2-pentyl-5,6-dimethylheptanol | 2.3 |
| <pre>      C<br>C C C C C C C C C C<br>        C  C*  C</pre> | 2-(3-methylbutyl)-4-methyloctanol | 2.2 |
| <pre>C C C C C C C C C C C C</pre> | 2-(1-methylbutyl)-nonanol | 1.5 |
| <pre>C C C C C C C C C C C C<br>              C*</pre> | 2-(1-methylbutyl)-nonanol | 1.5 |
| <pre>        C<br>C C C C C C C C C<br>    C   C*<br>    C</pre> | 2-(1-methylbutyl)-4-ethylheptanol | 0.7 |
| <pre>C C C C C C C C C C<br>      C   C*<br>      C</pre> | 2-pentyl-4-ethylheptanol | 0.6 |
| <pre>                C<br>C C C C C C C C C C<br>              C*  C</pre> | 2-(1,2-dimethylpropyl)-nonanol | 0.5 |
| <pre>            C<br>C C C C C C C C C C<br>        C   C*</pre> | 2-(1-methylbutyl)-4-methyloctanol | 0.4 |
| <pre>      C             C<br>C C C C C C C C C C<br>        C     C*  C</pre> | 2,(1,2-dimethylpropyl)-5,6-dimethylheptanol | 0.4 |
| <pre>C C C C C C C C C C<br>      C   C*    C<br>      C</pre> | 2-(3-methylbutyl)-4-ethylheptanol | 0.2 |
| <pre>              C<br>C C C C C C C C C C C<br>    C           C*  C</pre> | 2-(1,2-dimethylpropyl)-7-methyloctanol | UNK |

TABLE 3-continued

| Structure | Tetradecanols Name | Weight % |
|---|---|---|
| C<br>C C C C C C C C C<br>    C   C* C | 2-(1,2-dimethylpropyl)-5-methyloctanol | UNK |
| C<br>C C C C C C C C C<br>    C  C* C | 2-(1,2-dimethylpropyl)-4-methyloctanol | UNK |
| C<br>C C C C C C C C<br>    C  C* C | 2-(1,2-dimethylpropyl)-2-ethylheptanol | UNK |
| C C C C C C C C C C<br>    C  C*    C | 2-pentyl-4,6-dimethylheptanol | UNK |
| C C C C C C C C C C<br>  C   C   C*  C | 2-(3-methylbutyl)-4,6-dimethylheptanol | UNK |
| C<br>C C C C C C C C<br>  C  C  C* C | 2-(1,2-dimethylpropyl)-4,6-dimethylheptanol | UNK |
| C<br>C C C C C C C C C<br>  C  C  C* | 2-(1-methylbutyl)-4,6-dimethylheptanol | UNK |

Chromatographic retention times for particular alcohols, both as components of a mixture and from individual synthesis, are set forth in Table 4, together with the aldehyde pair involved in the synthesis.

Each of the individual alcohols in Tables 3 and 4, as well as the total mixture, can be converted to ethoxyl derivatives, sulfates, or ethoxyl sulfate derivatives. This is also the case with other alcohols described herein. Similarly, the individual enals and enal mixtures can be readily converted to saturated aldehydes, alcohols and acids.

TABLE 4

TETRADECANOLS GC IDENTIFICATION

| Name | Retention Time In Minutes | Aldol Condensation Substrates Carbanion | Acceptor | Retention Time From Individual Synthesis |
|---|---|---|---|---|
| 2-(3-methylbutyl)-5-methyloctanol | 31.99 | 5-methylhexanal | 3-methylhexanal | 32.36 |
| 2-(1-methylbutyl)-5-methyloctanol | 32.55<br>+<br>32.74 | 3-methylhexanal | 3-methylhexanal | 32.43<br>+<br>32.60 |
| 2-pentyl-5-methyloctanol | 36.62 | Heptanal | 3-methylhexanal | 36.49 |
| 2-(3-methylbutyl)-7-methyloctanol | 33.32 | 5-methylhexanal | 5-methylhexanal | 33.27 |
| 2-pentylnonanol | 43.60 | Heptanal | Heptanal | 43.44 |
| 2-(3-methylbutyl)-5,6-dimethylheptanol | 31.27 | 5-methylhexanal | 3,4-dimethylhexanal | 31.24 |
| 2-(1-methylbutyl)-5-,6-dimethylheptanol | 31.27 | 3-methylhexanal | 3,4-dimethylpentanal | 31.28 |
| 2-pentyl-7-methyloctanol | 37.86<br>or<br>38.18 | Heptanal | 5-methylhexanal | 37.93<br>or<br>38.29 |
| 2-(3-methylbutyl)-nonanol | 37.86<br>or<br>38.18 | 5-methylhexanal | Heptanal | 37.93<br>or<br>38.29 |
| 2-(1-methylbutyl)-7-methyloctanol | 34.17<br>+<br>34.40 | 3-methylhexanal | 5-methylhexanal | 34.31<br>+<br>34.50 |
| 2-pentyl-4-methyloctanol | 34.17<br>+<br>34.40 | Heptanal | 2-mrthylhexanal | 34.15<br>+<br>34.41 |
| 2-pentyl-5,6-dimethylheptanol | 35.79 | Heptanal | 3,4-dimethylpentanal | 35.82 |
| 2-(3-methylbutyl)-4-methyloctanol | 29.85<br>+<br>30.11 | 5-methylhexanal | 2-methylhexanal | 29.84<br>+<br>30.09 |
| 2-(1-methylbutyl)-nonanol | 38.98<br>+<br>39.13 | 3-methylhexanal | Heptanal | 38.89<br>+<br>39.04 |
| 2-(1-methylbutyl)-4-ethylheptanol | 26.67<br>+<br>26.95 | 3-methylhexanal | 2-ethylpentanal | 26.67<br>+<br>27.05 |
| 2-pentyl-4-ethylheptanol | 33.05 | Heptanal | 2-ethylpentanal | 32.97 |
| 2-(1,2-dimethylpropyl)-nonanol | 30.11 | 3,4-dimethylpentanal | Heptanal | 30.58 |
| 2-(1-methylbutyl)-4-methyloctanol | 30.40<br>+<br>30.84 | 3-methylhexanal | 2-methylhexanal | 30.38<br>+<br>30.83 |
| 2-(1,2-dimethylpropyl)-5,6-dimethylheptanol | 27.82<br>+<br>28.86 | 3,4-dimethylpentanal | 3,4-dimethylpentanal | 27.79<br>+<br>28.73 |

TABLE 4-continued
TETRADECANOLS GC IDENTIFICATION

| Name | Retention Time In Minutes | Aldol Condensation Substrates Carbanion | Acceptor | Retention Time From Individual Synthesis |
|---|---|---|---|---|
| | + 29.13 | | | + 29.01 |
| 2-(3-methylbutyl)-4-ethylheptanol | 28.86 | 5-methylhexanal | 2-ethylpentanl | 28.87 |
| | + 28.97 | | | + 28.89 |
| 2-(1,2-dimethylpropyl)-7-methyloctanol | | 3,4-dimethylpentanal | 5-methylhexanal | |
| 2-(1,2-dimethylpropyl)-5-methyloctanol | | 3,4-dimethylpentanal | 3-methylhexanal | |
| 2-(1,2-dimethylpropyl)-4-methyloctanol | | 3,4-dimethylpentanal | 2-methylhexanal | |
| 2-(1,2-dimethylpropyl)-2-ethylheptanol | | 3,4-dimethylpentanal | 2-ethylpentanal | |
| 2-pentyl-4,6-dimethylheptanol | | Heptanol | 2,4-dimethylpentanal | |
| 2-(3-methylbutyl)-4,6-dimethylheptanol | | 5-methylhexanal | 2,4-dimethylpentanal | |
| 2-(1,2-dimethylpropyl)-4,6-dimethylheptanol | | 3,4-dimethylpentanal | 2,4-dimethylpentanal | |
| 2-(1-methylbutyl)-4,6-dimethylheptanol | | 3-methylhexanal | 2,4-dimethylhexanal | |

Carbanion and acceptor columns present the two aldehydes that were used in aldos to prepare the respective alcohol.

The identification and reported percentage composition of the product alcohols were accomplished by utilizing gas-liquid chromatography (G.C.) coupled with synthesis of the isomers. The individual alcohols were synthesized by aldol condensation of pure heptanal aldehyde isomers followed by hydrogenation to the alcohol. The heptanal pairs can be reacted together with the procedure of Example 7 above. The elution time of the individual derivatized isomers were then matched with peak-elution times in the product mixture to identify the compounds in the mixture. Verification of the structures was accomplished by several methods. Gas chromatography combined with mass spectrometry (G.C. - MS) was used to show that the mixture contained only tetradecanol isomers. The logic by which we synthesized the various alcohol isomers, discussed above, was confirmed in three cases by $^{13}C$ nuclear magnetic resonance (nmr) and also in one case by a single crystal X-ray structural determination of a solid derivative. Thus, the structures of 2-pentylnonanol, 2-(1-methybutyl-5-methyl-octanol and 2-(3-methylbutyl) 7-methyloctanol were unambiguously identified using two dimensional double quantum coherence $^{13}C$ nmr techniques (G. Bodenhause, "Progress in NMR Spectrocscopy," 14 , 137 (1981). In addition, the -napthyl sulfonate ester of 2-(3-methylbutyl-7-methyl octanol was prepared (m. pt 47°) and a single crystal suitable for X-ray crystallographic investigation was grown. A single crystal study was performed using copper K radiation with a Syntex P2₁ diffractometer. The space group was found to be P2₁/N. Cell constants were=8.186(1), b=29.958 (7), c=10.316(2) A; a=107.49(2)°; Z=4; M=404.62. The structure was solved by direct methods and refined to a final ⓡ value of 0.091 using 2586 observed reflections. The structure is shown in the accompanying FIG. 1. The bond lengths and bond angles are given in Table 5.

This X-ray determination unequivocably confirms the backbone structure of the alcohol as 2-(3-methylbutyl)7-methyl octanol.

TABLE 5
Bond Lengths and Bond Angles in the -Naphthyl Sulfonate Ester of 2-(3-methylbutyl-7-methyl Octanol
(Numbering system used here is shown in FIG. 1)

Bond Lengths

| | | | |
|---|---|---|---|
| S1 | — | 02 | 1.565 A |
| S1 | — | 011 | 1.427 |
| S1 | — | 012 | 1.427 |
| 02 | — | C3 | 1.493 |
| C3 | — | C4 | 1.543 |
| C4 | — | C5 | 1.526 |
| C4 | — | C23 | 1.538 |
| C5 | — | C6 | 1.534 |
| C6 | — | C7 | 1.542 |
| C7 | — | C8 | 1.544 |
| C8 | — | C9 | 1.573 |
| C9 | — | C10 | 1.574 |
| S1 | — | C14 | 1.747 |
| C13 | — | C14 | 1.392 |
| C13 | — | C18 | 1.399 |
| C14 | — | C15 | 1.421 |
| C15 | — | C16 | 1.347 |
| C16 | — | C17 | 1.416 |
| C17 | — | C22 | 1.417 |
| C18 | — | C19 | 1.442 |
| C20 | — | C21 | 1.449 |
| C21 | — | C22 | 1.372 |
| C23 | — | C24 | 1.545 |
| C24 | — | C25 | 1.564 |
| C25 | — | C26 | 1.540 |
| C25 | — | C27 | 1.393 |

Bond Angles

| | | | | | |
|---|---|---|---|---|---|
| 02 | — | S1 | — | 011 | 104.1° |
| 02 | — | S1 | — | 012 | 109.8 |
| 02 | — | S1 | — | C14 | 103.3 |
| 011 | — | S1 | — | 012 | 119.9 |
| 011 | — | S1 | — | C14 | 108.9 |
| 012 | — | S1 | — | C14 | 109.5 |
| S1 | — | 02 | — | C3 | 117.9 |
| 02 | — | C3 | — | C4 | 106.0 |
| C3 | — | C4 | — | C5 | 111.4 |
| C3 | — | C4 | — | C23 | 113.2 |
| C5 | — | C4 | — | C23 | 109.4 |
| C4 | — | C5 | — | C6 | 115.8 |
| C5 | — | C6 | — | C7 | 110.1 |
| C6 | — | C7 | — | C8 | 110.6 |
| C7 | — | C8 | — | C9 | 111.7 |
| C8 | — | C9 | — | C10 | 112.5 |
| C8 | — | C9 | — | C28 | 106.8 |
| C10 | — | C9 | — | C28 | 112.4 |
| C14 | — | C13 | — | C18 | 118.6 |
| S1 | — | C14 | — | C13 | 119.9 |
| S1 | — | C14 | — | C15 | 118.6 |
| C13 | — | C14 | — | C15 | 121.6 |
| C14 | — | C15 | — | C16 | 119.6 |
| C15 | — | C16 | — | C17 | 121.5 |
| C16 | — | C17 | — | C18 | 118.4 |
| C16 | — | C17 | — | C22 | 122.5 |
| C18 | — | C17 | — | C22 | 119.1 |
| C13 | — | C18 | — | C17 | 120.3 |
| C13 | — | C18 | — | C19 | 120.0 |
| C17 | — | C18 | — | C19 | 119.6 |
| C18 | — | C19 | — | C20 | 119.8 |
| C19 | — | C20 | — | C21 | 120.2 |
| C20 | — | C21 | — | C22 | 120.6 |
| C17 | — | C22 | — | C21 | 120.6 |

TABLE 5-continued

Bond Lengths and Bond Angles in the -Naphthyl Sulfonate Ester of 2-(3-methylbutyl-7-methyl Octanol (Numbering system used here is shown in FIG. 1)

| | | | | | |
|---|---|---|---|---|---|
| C4 | — | C23 | — | C24 | 113.6 |
| C23 | — | C24 | — | C25 | 112.1 |
| C24 | — | C25 | — | C26 | 108.2 |
| C24 | — | C25 | — | C27 | 119.2 |
| C26 | — | C25 | — | C27 | 114.3 |

In FIG. 1, the βnapthylsulfonate ester of 2-(3-methylbutyl)-7-methyl octanol is shown. The sulfur and oxygen atoms are identified by as S and O respectively, while all other atoms are carbon. The portion of the structure below the oxygen atom 2 is the carbon structure of the alcohol, while that above 2 is the naphthylsulfonate portion of the derivative.

The gas chromatography for the retention procedures discussed was done with acetate ester derivatives. The acetate esters were prepared by utilizing 0.1 cc of alcohol sample, 0.3 cc acetic anhydride, 1 drop of pyridine, and heating in a sealed vial for 10 minutes at 100° C. The product was injected directly into a gas chromatogram, which was a Varian 3700 with splitter for glass capillary columns, Flame ionization detector and Hewlett-Packard 3352 computer. Details of the column and procedure were:

SP-2100 Glass capillary column 60 meter length×0.25 mm internal diameter, 27.1 cm/sec helium;
Injection/splitter: 280° C.
Detector: 280° C.
Column oven: Progress from 120° C. to 150° C. at 2° C./minute, and held at 150° C.
Detector Sensitivity: Range $10^{-11}$ amps/millimole
Injection Size: 0.06 ul/split 60:1

Figure 2:
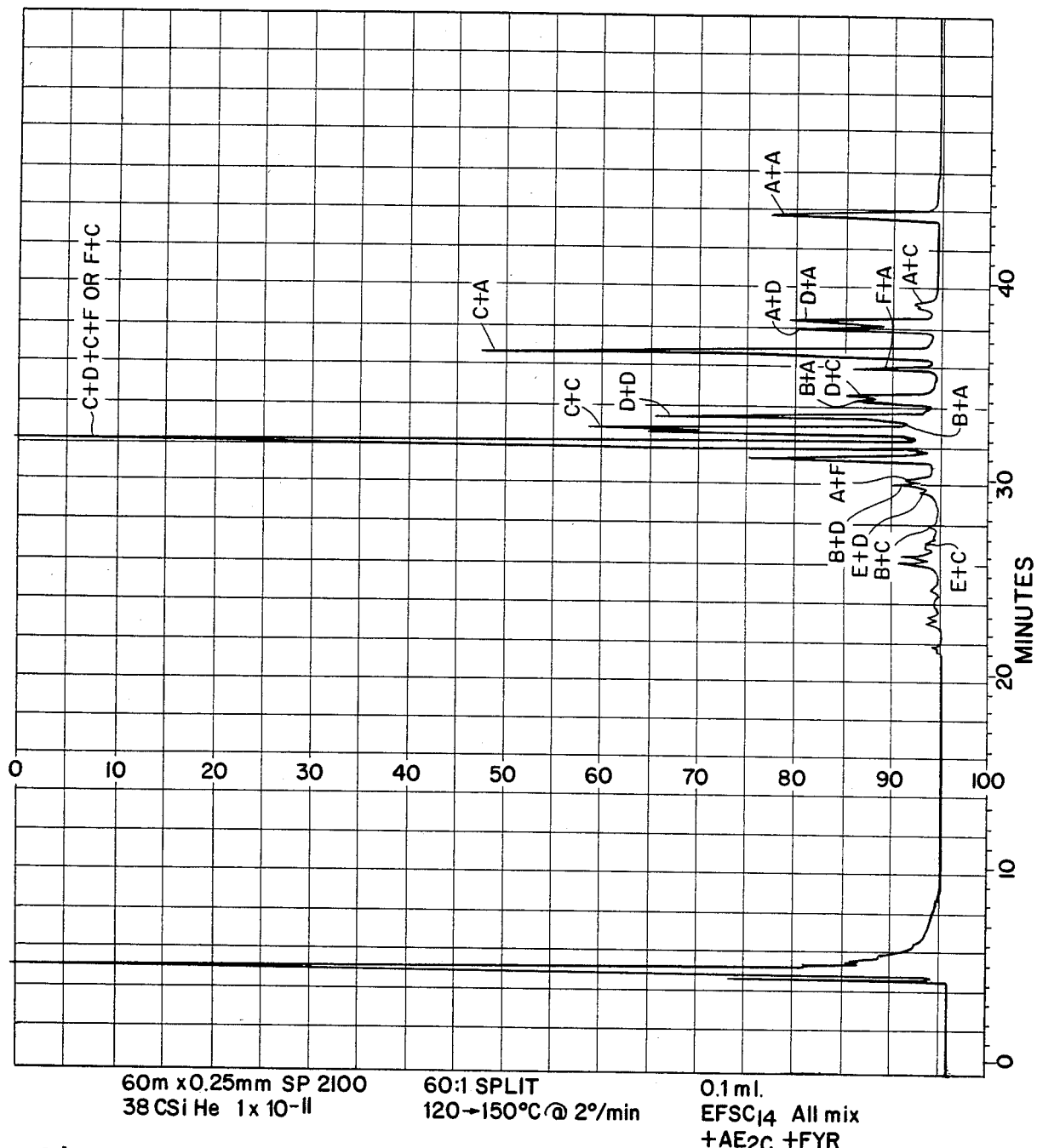

A typical chromatograph of the acetate derivative of the mixture of alcohols of Table 3, obtained by the foregoing procedure, is shown in FIG. 2 in which retention time is measured on the horizontal axis in minutes. The chromatograph was made at a chart speed of 5 mm/minute and covers from time zero to over 50 minutes. The designations of several peaks by combinations of two letters indicate the aldehydes combined in the aldol stage of the product formation, with the letters symbolizing:

A = n-heptanal
B = 2-methylhexanal
C = 3-methylhexanal
D = 4-methylhexanal
E = 2-ethylpentanal
F = 2,3-dimethylpentanal

EXAMPLE 9

This example demonstrates an aldol condensation of heptanal in glassware under conventional aldol conditions. The reaction flask was charged with 116 ml of 0.8 M NaOH and the heptanal, 371.03 g., placed into the addition funnel. The system was kept under a nitrogen blanket and the agitation was set at 500 rpm. The reaction flask was heated to reflux, and the heptanal added at a constant rate such that the addition was completed after 230 minutes. A sample was removed to compare with conventional aldol results and only 33.5% of the upper phase of the sample was $C_{14}$ unsaturated aldehyde and 61% was unreacted heptanal. The system was held at reflux for an additional 10 hours after which the system was cooled. The lower phase was removed, 135.74 g, and the upper phase, 336.06 g., was found to contain 66.5% 2-pentylnon-2-enal, 26.4% unreacted heptanal and 2.5% heptanol.

EXAMPLE 10

This example demonstrates the efficacy of using a co-solvent with the water to enhance the aldol reaction of heptanal. The reaction flask was charged with 31 ml of 0.9 M NaOH and 100 ml methanol. The addition funnel was charged with 115 g. of heptanal under a nitrogen blanket. The aqueous-methanol mixture was heated to reflux with agitation of 450 rpm. The heptanal was added over a 40 minute period and refluxed for an additional 90 minutes. The system was cooled and the lower phase removed. The upper phase contains 10.1% methanol, 84.0% 2-pentylnon-2-enal, 2.0% unreacted heptanal and 1.2% heptanol. This represents 94% conversion with 98% selectivity. The tetradecenals were hydrogenated as in Example 8 and the resulting saturated alcohols were treated as in example 8 including filtration and distillation.

The use of methanol in this procedure was effective as a cosolvent, as compared to Example 9 where a cosolvent was not used.

EXAMPLE 11

Dimerization of propylene over transition metal catalysts produces a mixture of hexenes.

The linear hexenes in the mixture can be separated and such linear hexenes are for the most part 2-hexenes. The folloing procedure illustrates the reaction of linear 2-hexenes in an oxo reaction, followed by an aldol reaction of the product. A sample of refinery 2-hexenes was passed through basic alumina particles for removal of oxides and 802 grams of the hexenes was placed in a 1 gallon stainless steel autoclave with 4.75 grams $Co_2(CO)_8$ catalyst. The autoclave was pressured to 2400 psi gauge with 1:1 carbon monoxide and hydrogen, and heated to 110° C. The temperature was kept at about 110° C. for 1 hour and then rose to about 130° as the procedure was continued for about 5 hours. A 916.5 gram product was obtained, with conversion about 94% with about 78% selectivity to $C_7$ compounds, and 71.5% to $C_7$ aldehydes. Chromatography indicated the aldehydes were in ratio of about 29.4 n-heptanal to 16.7 2-methylhexanal to 8.5 2-ethylpentanal. A 907 gram amount of the product was distilled, with a final pot temperature of 120° C. and vacuum of 3 mm Hg. to obtain a 608 gram distillation fraction and 278 gram residue. Chromatography indicated the fraction included $C_7$ aldehydes in ratio 33.4 n-heptanal to 26.8 2-methylhexanal to 17.2 2-ethylpentanal, and minor amounts of other components. Evidently there was more loss of the normal aldehyde than the branched ones in the distillation.

It is feasible to achieve a higher percentage of n-aldehyde than present in the above distillation fraction, such as 60% or better, and therefore n-heptanal was added to the above fraction to have a more typical aldehyde for aldol reaction about 600 grams of the above fraction being used with 500 grams n-heptanal. A 300 ml amount of 0.8 molar sodium hydroxide was placed in a reaction flask with 955 ml methanol, and the aldehydes were placed in an addition funnel. The reaction medium was heated to about 71° C., and addition was slowly started and completed in about 13 hours. Chromatography indicated about 50% completion of the reaction, with $C_{14}$ aldehydes in ratio of about 23.4% 2-pentylnon-2-enal to 8.72% 2-penthyl-4-methyloct-2-enal to 1.4%

2-pentyl-4-ethylhept-2-enal. Several $C_7$ aldehydes were also present in the ratio of 22.0 heptanal to 8.5 2-methylhexanal to 5.3 2-ethylpentanal.

The aldol condensation product was hydrogenated over a cobalt on Kieselguhr catalyst, using 131 grams catalyst with 1336 grams of the condensation product. The materials were maintained at about 160° C. and 1500 psi gauge (10,645 KPa) of hydrogen for about two hours when reaction appeared complete. Reaction conditions were maintained for an additional 4.5 hours. Analysis indicated about 99% completion of the hydrogenation. The product contained 2-pentyl-nonanol in about 18.4 to 7.2 ratio to a mixture of 2-pentyl-5-methyl-octanol and 2-pentyl-4-ethyl-heptanol and large amounts of $C_7$ alcohols from the unreacted aldehyde, being heptanol in a 27.5 to 16.3 ratio to a mixture of 2-methylhexanol and 2-ethylpentanol. The product was fractionated by distillation, with a 280 gram fraction being obtained at 110°-115° C. at 2 mm Hg from 1180 grams of hydrogenation product. The fraction was in large predominance composed of $C_{14}$ alcohols.

EXAMPLE 12

A mixture of hexenes produced by the Dimersol ® dimerization process was utilized as olefin reactant. The crude hexene cut from the dimerization was used, and had the distribution of linear and branched hexenes typical of such material. A 1029 gram amount of the hexenes was used in a 1 gallon autoclave with 6.04 grams catalyst, $Co_2(CO)_8$, 0.02 weight %. Peroxides had been removed from the hexenes by treatment on a basic alumina column. The autoclave was taken to reaction conditions with 1:1 $CO/H_2$ and maintained at 110° C. and 2600 psi gauge (18028 KPa) for 9 hours, with 80% of theoretical gas uptake, and then continued overnight. Chromatography indicated high conversion to $C_7$ aldehydes, with minor amounts of residual hexenes. A 1360 gram amount of the product was subjected to distillation, with a 797 gram fraction being obtained at pot temperatures of 60° to 97° C. as the vacuum dropped from 90 mm Hg to 5 mm Hg. Chromatography indicated a high portion of $C_7$ aldehydes with a very small amount of $C_6$ olefins.

A 792 gram amount of the above aldehyde fraction was utilized in an aldol reaction, adding the aldehyde material from an addition funnel to a reaction flask containing 564 grams methanol and 250.9 grams 0.8 molar sodium hydroxide. The addition took 6 hours, with stirring at about 500 rpm and temperature at 72°-73° C. The reaction mixture was then refluxed for 1.5 hours. Analysis of a sample indicated only about 1 part aldol product to 3 parts aldehyde, on a mole basis. The reaction was continued at reflux overnight, giving 1 part aldol product to about 2.6 parts aldehyde reactant. During the reaction it was observed that the reaction mixture had a large upper phase and a smaller lower phase, indicating that methanol was not very effective in promoting miscibility and reaction, possibly because of the relatively long chain length of $C_7$ aldehydes. Chromatography showed a fair amount of the $C_{14}$ aldol product, including 2-pentylnonenal, and a large amount of unreacted $C_7$ aldehydes. (Results were better in Example 10 above in which a higher proportion of methanol was employed).

The above aldol product was subjected to further aldol reaction, after removing the methanol to employ different conditions. A 552 gram amount of the aldol condensate, 55.6 area percent $C_7$ aldehydes and 31.5 area percent $C_{14}$ enals, was placed in an addition funnel and added to a reaction flask containing 163 grams 0.8M NaOH and 389 grams 2,5-hexanediol. Addition was complete after 45 minutes, with temperature maintained at 100° C. with agitation of the reaction mixture. The reaction mixture was then refluxed at 100° C. for 1.75 hours. The reaction mixture separated into upper and lower phases of about equal weight. The conversion had been improved in that the ratio of $C_{14}$ enals to $C_7$ aldehydes in the product (upper phase) was now about 1.7 to 1.

A 515 gram amount of the product was subjected to hydrogenation, employing 51.65 grams cobalt on Kieselguhr catalyst and 160° C., about 1580 psi gauge (10,995 KPa) hydrogen. Approximately 549 grams of product was recovered. The conversion of $C_{14}$ saturated alcohols was about 90%, with about 10% found as unsaturated alcohols. The product was filtered to remove catalyst, and the filtrate was distilled. The process produced several $C_{14}$ alcohols in very substantial amounts, with a number of others in very small amounts. Several $C_7$ alcohols from unreacted aldehyde were also present in substantial amount.

EXAMPLE 13

A freshly distilled sample of 2-pentene was hydroformylated in a 300 ml autoclave, employing 0.41 gram $Co(CO)_8$ catalyst with 65.84 grams pentene. A 1:1 mixture of $CO/H_2$ was used, with initial charge to 1500 psi gauge and heating to 120° C. and 3000 psi. with agitation at 1000 rpm. Gas-uptake was observed, as the pressure was increased to 3000 psi (20,684 KPa) After about 2 hours, an 83 gram product was obtained. Chromatography showed a small residual amount of pentene and $C_6$ aldehydes in the ratio of 61.1 hexanal to 28.9 2-methylpentanal to 10.0 2-ethylbutanal. An aldehyde sample was provided to have aldehydes in the same ratio, using 189.1 grams hexanal, 89.9 grams. 2-methylpentanal, and 31 grams 2-ethylbutanal, and placed in an addition funnel for addition to 110 ml of 0.8 M NaOH in a round bottom flask equipped with a mechanical stirrer. Heating was begun and addition was started after about 15 minutes and continued as reflux started around 91° C. Addition was completed in about 40 minutes. Stirring was continued for an hour, but without further heating, and a sample was taken. Analysis indicated partial reaction. The reaction mixture was heated to 95° C. for an additional 1½ hours. Upper and lower phases of the reaction mixture were separated, and the upper phase was analyzed. The analysis indicated better than 25% conversion to $C_{12}$ enal, nearly all being 2-butyloctanal, and large amounts of unreacted $C_6$ aldehydes, the major part of which was branched aldehydes. The aldehyde mixture can readily be hydrogenated to the corresponding alcohols.

EXAMPLE 14

An aldol procedure was carried out as in Example 13 except that the amount of water was increased ten fold. The same amount of NaOH was present, although now in much more dilute solution. Because of the large volume, less effective stirring was achieved. After a two hour reaction, analysis indicated substantial conversion to $C_{12}$ enals, although somewhat lower than in Example 12.

EXAMPLE 15

An aldol reaction was carried out as in Example 13, employing 6.1 to 2.9 to 1 ratio of hexanal to 2-methylpentanal to 2-ethylbutanal, the total amount being 310 grams. The branched aldehydes were placed in a flask with 110 ml of 0.8 M NaOH, and tetrabutylammonium chloride in an amount molecularly equivalent to the NaOH. The tetrabutyl-ammonium chloride serves as a phase transfer catalyst. The reaction flask was heated to reflux and addition was started. The addition continued for about 6 hours with reflux temperatures (pot) from 90°–95° C. The mixture was cooled and separated into two phases. Analysis of the upper phase showed better than 75% conversion to $C_{12}$ enals, about half of which was 2-butyloctenal, and the remainder mainly a mixture of 2-butyl-4-ethyl-heptenal and 2-butyl-4-ethylhexenal. In the unreacted $C_6$ aldehydes present, the branched aldehydes were in greater amount the hexanal. The reaction can be directed to produce a higher percentage of product from the n-hexanal by adding the aldehydes together, rather than adding the n-aldehyde to the branched aldehydes in the reaction mixture as in the foregoing procedure. The phase transfer catalyst was effective in improving conversion in this procedure, but use of co-solvents, such as methanol or diols, may be more practical for large scale continuous operations. The use of hexanediol has been shown effective for aldol reaction of heptanals herein, and can similarly be used with hexanals.

It will be noted that the alcohols produced from both the pentenes and hexenes feedstocks are intended for use as detergent range alcohols. The considerations herein as to reaction conditions and various parameters of the oxo and aldol reactions as decribed for the hexenes and resulting $C_7$ aldehydes also are in general applicable to the pentenes and resulting $C_6$ aldehydes. The $C_{12}$ alcohols produced from the reactions starting with pentenes will have the hydrophobic groups such alcohols provide in detergents, and the groups will have a degree of branching similar to that of $C_{14}$ alcohols from hexenes. It is feasible to substantially avoid presence of branches on adjacent carbon atoms. In one particular aspect the present invention is directed to a process of preparing alcohols from an oxo reaction with olefins selected from those having 5 to 6 carbon atoms, or mixtures thereof, to obtain aldehydes having 6 to 7 carbon atoms, comprising high amounts of aldehydes without 2-substitution and effecting aldol conversion with limited participation of 2-substituted aldehyde to obtain aldol product, which is then hydrogenated to $C_{12}$ or $C_{14}$ alcohols having properties valuable for use in detergents.

EXAMPLE 16

An aldol reaction was conducted in a 1 liter round bottom flask equipped with stirrer, addition funnel, reflux condenser and adaptors for nitrogen flow. A 100 ml. amount of aqueous 1 molar potassium hydroxide solution was placed in the flask and heated to about 85° C. n-Pentanal and 2-methylbutanal were admixed in about 3:1 ratio, after each had been purified by distillation, and used for gradual addition to the reaction flask with stirring. Over about one hour, about 300 ml was added containing 187.7 grams n-pentanal and 60.8 grams 2-methylbutanal. The reaction mixture was placed in a separatory funnel; and the lower aqueous phase (87 grams) was separated. The organic layer was washed four times with water and amounted to 213.3 grams. Gas chromatographic analysis for the starting aldehydes indicated about a 3:1 ratio of 2-methylbutanal to n-pentanal, showing that the n-pentanal had been consumed at a much higher rate in the reaction. The product contained about 70.5% of alkenal condensation product and 25.3% of the starting aldehydes. The product had 2-propyl-heptanal in about 9:1 ratio to 2-propyl-4-methyl-hexanal.

A 110.89 gram amount of the product was utilized for hydrogenation, employing 11 grams of cobalt on Kieselguhr catalyst with 4.4 ml $H_2O$ as promoter, in a 300 ml strrred autoclave. The autoclave was pressured to 1000 psi with hydrogen and gradually heated, with hydrogen uptake starting at about 40° C. After one hour, the pressure had fallen to 480 psi, and the autoclave was again pressured to 1000 psi. After two hours, with further addition of hydrogen, the pressure was 1510 psi and temperature 160° C. The run was continued for a total of sixteen hours. The measured gas uptake was in very slight excess of theory for hydrogenation of both the olefin and aldehyde groups in the compounds present.

The product was filtered through a Celite filter mat to remove catalyst, and the mat was washed with n-hexane. The n-hexane was removed under vacuum, leaving 88 grams of product for distillation. Distillation was carried out at 10 mm Hg., with 18.1 gram being collected at 30°–100° C., which gas chromatography indicated to be 66.4% 2-methylbutanol, 27.5% pentanol, and 4.1% 2-propylheptanol. An additional 38.9 grams was collected at 103.5°–105° C., 11.3% 2-propyl-4-methylhexanol and 87.7% 2-propylheptanol. It can be seen that the above described procedure provides 2-propylheptanol with only very minor adulteration by the aldol alcohols product of branched aldehydes. Also the 2-propylheptanol from the 2-methylbutanol produced by hydrogenation of the 2-methylbutanal which did not undergo the aldol condensation.

Another sample of hexenes product from a Dimersol ® dimerization refinery product was analyzed and found to have the following distribution:

| Hexene Distribution | |  |
|---|---|---|
| | % (100% Basis) | |
| 2,3-dimethyl-2-butene | 6.4 | |
| 2-methyl-2-pentene | 39.2 | |
| trans-4-methyl-2-pentene | 15.9 | |
| cis-4-methyl-2-pentene | 2.9 | |
| 2-methyl-1-pentene | 5.0 | |
| 2,3-dimethyl-1-butene + 4-methyl-pentene-1 | 1.7 | |
| trans-2-hexene | 16.5 | |
| trans-3-hexene | 5.8 | 28.9% |
| cis + cis 2-hexene | 5.6 | |
| 1-hexene | 1.0 | |

The hexenes are suitable for conversion to detergent alcohol in accord with the present invention.

EXAMPLE 17

An aldehyde mixture representative of that from the oxo reaction of Dimate ® hexenes, as described in Example 1, was reacted in an aldol condensation. A stirred autoclave was charged with 735 ml 0.8M NaOH, 1470 ml methanol and 20 psig argon (KPa). The autoclave was heated to 100° C. and 735 ml (551.0g) of the aldehydes were pressurized into the autoclave with argon.

The reaction was run for an additional hour and the system was rapidly cooled. The product was removed and the upper and lower phases were separated. The upper phase contained 14.4% unreacted aldehydes, 2.1% heptanols, 4.4% methanol, 1.6% high boilers and 77.5% tetradecenals. The tetradecenals product consists of some 28 isomers in amounts as named and illustrated in Table 5 where the aldehydic function is designated by an asterisk.

TABLE 5
2-TETRADECENALS FROM OXO AND ALDOL OF DIMATE HEXENES

| STRUCTURE | COMPOUND NAME | WEIGHT % | ALDOL CONDENSATION SUBSTRATES CARBANION | ACCEPTOR |
|---|---|---|---|---|
| 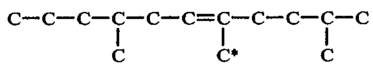 | (E + Z)-2-(3-METHYLBUTYL)-5-METHYL-2-OCTENAL | 25.4 | 5-METHYLHEXANAL | 3-METHYLHEXANAL |
| 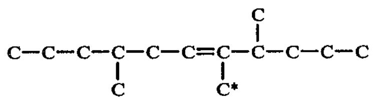 | (E + Z)-2-(1-METHYLBUTYL)-5-METHYL-2-OCTENAL | 14.8 | 3-METHYLHEXANAL | 3-METHYLHEXANAL |
| 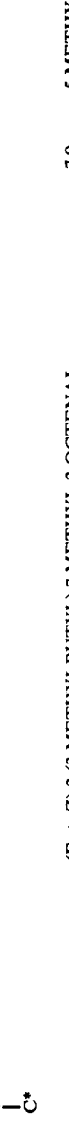 | (E + Z)-2-PENTYL-5-METHYL-2-OCTENAL | 13.4 | HEPTANAL | 3-METHYLHEXANAL |
| 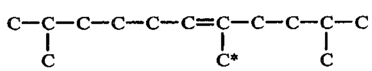 | (E + Z)-2-(3-METHYLBUTYL)-7-METHYL-2-OCTENAL | 7.0 | 5-METHYLHEXANAL | 5-METHYLHEXANAL |
| 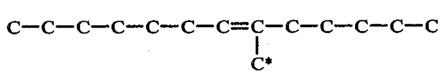 | (E + Z)-2-PENTYL-2-NONENAL | 6.0 | HEPTANAL | HEPTANAL |
| 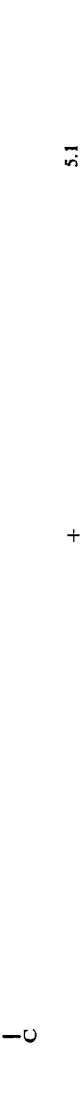 | (E + Z)-2-(3-METHYLBUTYL)-5,6-DIMETHYL-2-HEPTENAL + (E + Z)-2-(1-METHYLBUTYL)-5,6-DIMETHYL-2-HEPTENAL | 5.1 | 5-METHYLHEXANAL 3-METHYLHEXANAL | 3,4-DIMETHYLPENTANAL 3,4-DIMETHYLPENTANAL |
| 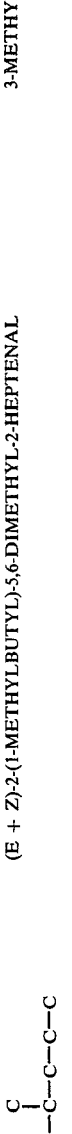 | (E + Z)-2-PENTYL-7-METHYL-2-OCTENAL | 4.1 | HEPTANAL | 5-METHYLHEXANAL |
| 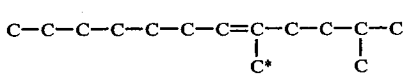 | (E + Z)-2-(3-METHYLBUTYL)-2-NONENAL | 4.1 | 5-METHYLHEXANAL | HEPTANAL |
| 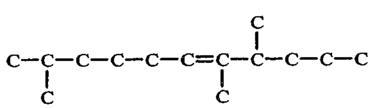 | (E + Z)-2-(1-METHYLBUTYL)-7-METHYL-2-OCTENAL | 2.4 | 3-METHYLHEXANAL | 5-METHYLHEXANAL |

TABLE 5-continued

2-TETRADECENALS FROM OXO AND ALDOL OF DIMATE HEXENES

| COMPOUND | | | ALDOL CONDENSATION SUBSTRATES | |
|---|---|---|---|---|
| NAME | STRUCTURE | WEIGHT % | CARBANION | ACCEPTOR |
| (E + Z)-2-PENTYL-4-METHYL-2-OCTENAL | C—C—C—C—C=C—C—C—C—C<br>                                      C—C* | 2.4 | HEPTANAL | 2-METHYLHEXANAL |
| (E + Z)-2-PENTYL-5,6-DIMETHYL-2-HEPTENAL | C—C—C—C—C=C—C—C—C—C<br>                               C—C—C*<br>                                   C | 2.3 | HEPTANAL | 3,4-DIMETHYLPENTANAL |
| (E + Z)-2-(3-METHYLBUTYL)-4-METHYL-2-OCTENAL | C—C—C—C—C=C—C—C—C—C<br>                           C—C*<br>                         C | 2.2 | 5-METHYLHEXANAL | 2-METHYLHEXANAL |
| (E + Z)-2-(1-METHYLBUTYL)-2-NONENAL | C—C—C—C—C—C—C=C—C—C<br>                               C—C—C*<br>                                   C | 1.5 | 3-METHYLHEXANAL | HEPTANAL |
| (E + Z)-2-(1-METHYLBUTYL)-4-ETHYL-2-HEPTANAL | C—C—C—C=C—C—C—C—C<br>             C<br>           C—C—C*<br>                C | 0.7 | 3-METHYLHEXANAL | 2-ETHYLPENTANAL |
| (E + Z)-2-PENTYL-4-ETHYL-2-HEPTENAL | C—C—C—C—C=C—C—C—C<br>                           C—C*<br>                         C—C | 0.6 | HEPTANAL | 2-ETHYLPENTANAL |
| (E + Z)-2-(1,2-DIMETHYLPROPYL)-2-NONENAL | C—C—C—C—C—C—C=C—C—C<br>                               C—C*<br>                               C—C | 0.5 | 3,4-DIMETHYLPENTANAL | HEPTANAL |
| (E + Z)-2-(1-METHYLBUTYL)-4-METHYL-2-OCTENAL | C—C—C—C—C=C—C—C—C<br>                    C<br>                    C—C—C*<br>                             C | 0.4 | 3-METHYLHEXANAL | 2-METHYLHEXANAL |
| (E + Z)-2-(3-METHYLBUTYL)-4-ETHYL-2-HEPTENAL | C—C—C—C=C—C—C—C—C<br>                         C—C*<br>                         C—C | 0.2 | 5-METHYLHEXANAL | 2-ETHYLPENTANAL |
| (E + Z)-2-(1,2-DIMETHYLPROPYL)-5,6-DIMETHYL-2-HEPTENAL | C—C—C—C=C—C—C—C<br>C—C                      C—C*<br>                            C | UNK | 3,4-DIMETHYLPENTANAL | 3,4-DIMETHYLPENTANAL |

TABLE 5-continued

2-TETRADECENALS FROM OXO AND ALDOL OF DIMATE HEXENES

| STRUCTURE | COMPOUND NAME | WEIGHT % | ALDOL CONDENSATION SUBSTRATES CARBANION | ACCEPTOR |
|---|---|---|---|---|
| C—C—C—C—C—C=C—C—C<br>                   C—C*<br>                   C | (E + Z)-2-(1,2-DIMETHYLPROPYL)-7-METHYL-2-OCTENAL | UNK | 3,4-DIMETHYLPENTANAL | 5-METHYLHEXANAL |
| C—C—C—C—C—C=C—C—C<br>                   C—C*<br>    C | (E + Z)-2-(1,2-DIMETHYLPROPYL)-5-METHYL-2-OCTENAL | UNK | 3,4-DIMETHYLPENTANAL | 3-METHYLHEXANAL |
| C—C—C—C—C=C—C—C<br>               C—C*<br>   C | (E + Z)-2-(1,2-DIMETHYLPROPYL)-4-METHYL-2-OCTENAL | UNK | 3,4-DIMETHYLPENTANAL | 2-METHYLHEXANAL |
| C—C—C—C—C=C—C—C<br>             C—C*<br>    C—C | (E + Z)-2-(1,2-DIMETHYLPROPYL)-2-ETHYL-2-HEPTENAL | UNK | 3,4-DIMETHYLPENTANAL | 2-ETHYLPENTANAL |
| C—C—C—C—C=C—C—C—C<br>               C—C*<br>          C | (E + Z)-2-PENTYL-4,6-DIMETHYL-2-HEPTENAL | UNK | HEPTANAL | 2,4-DIMETHYLPENTANAL |
| C—C—C—C—C=C—C—C<br>       C—C—C*<br>          C | (E + Z)-2-(3-METHYLBUTYL)-4,6-DIMETHYL-2-HEPTENAL | UNK | 5-METHYLHEXANAL | 2,4-DIMETHYLPENTANAL |
| C—C—C—C—C=C—C—C<br>    C—C—C*<br>         C | (E + Z)-2-(1,2-DIMETHYLPROPYL)-4,6-DIMETHYL-2-HEPTENAL | UNK | 3,4-DIMETHYLPENTANAL | 2,4-DIMETHYLPENTANAL |
| C—C—C—C=C—C—C—C<br>          C—C*<br>    C | (E + Z)-2-(1-METHYLBUTYL)-4,6-DIMETHYL-2-HEPTENAL | UNK | 3-METHYLHEXANAL | 2,4-DIMETHYLHEXANAL |
| | TOTAL | 93.1 | | |

CARBANION AND ACCEPTOR COLUMNS PRESENT THE TWO ALDEHYDES THAT WERE USED IN ALDOLS TO PREPARE THE TETRADEC-2-ENALS LISTED.

EXAMPLE 18

This experiment and Example 19 illustrates the utility of the invention for mixtures of olefins. Hydroformylation of Dimate ® hexenes and butenes was carried out in an autoclave with agitation. The autoclave was charged with 2.61 g of dicobalt octacarbonyl(catalyst precursor), 270.2 g of Dimate ® hexenes and 180.9 g butenes and 3000 psi gauge (20.786 KPa) of 1:1 CO and $H_2$. The autoclave was heated to 120° C. and held for two hours. The autoclave and contants were cooled rapidly and the product removed under argon. The product was analyzed chromatographically as reported in Table 6.

TABLE 6

| Dimate ® hexene, butene-2 Hydroformylation Products | |
|---|---|
| Compound | Area % |
| Butene-2 | 1.5 |
| Dimate hexenes | 9.6 |
| 2,2-dimethylpentanal | 0.5 |
| 2,4-dimethylpentanal | 2.1 |
| 2-methylbutanal | 10.0 |
| Pentanal | 23.6 |
| 2-ethyl-3-methylbutanal | 0.4 |
| 2-ethylpentanal | 3.3 |
| 3,4-dimethyllpenntanal | 0.5 |
| 2-methylhexanal | 3.2 |
| 3-methylhexanal | 18.5 |
| 5-methylhexanal | 12.5 |

TABLE 6-continued

| Dimate ® hexene, butene-2 Hydroformylation Products | |
|---|---|
| Compound | Area % |
| Heptanal | 9.3 |
| High Boilers (including heptyl alcohols and Formates) | 5.0 |

The percent of aldehyde production without 2-substitution was over 76%.

EXAMPLE 19

An aldehyde mixture representative of that from the oxo reaction of Dimate ® hexenes and butene as described in Example 18 was reacted in an aldol condensation. A stirred autoclave was charged with 313 ml methanol, 0.8M NaOH, and 110 psi (758.4 KPa) gauge argon. The system was heated to 100° C. and the mixture of aldehydes, 313 ml, was pressured into the autoclave with argon. The reaction was run an additional one hour and thirty minutes and the system rapidly cooled. The product was removed and the upper phase and lower phases were separated. The upper phase contained 0.5% unreacted pentanals, 31.7% unreacted heptanals, 25.6% decenals, 27.1% 2-dodecenals, 6.3% 2-tetradecenals, 1.7% pentanals, 6.3% heptanals and 0.8% high boilers. The skeletal structures of the 2-decenals and the 2-dodecenals are given in TABLE 7. The enals can readily be converted to alcohols and ethoxyl, sulfate or ethoxylsulfate derivatives.

TABLE 7

2-DECENALS AND 2-DODECENALS FROM ALDOL OF PENTANAL AND DIMATE HEXENES HEPTANALS

| STRUCTURE | COMPOUND NAME |
|---|---|
| C—C—C—C—C=C—C—C—C<br>　　　　　　｜<br>　　　　　　C | (E + Z)-2-PROPYL-2-HEPTENAL |

2-DODECENALS

| STRUCTURE | COMPOUND NAME |
|---|---|
| C—C—C—C—C—C—C=C—C—C—C<br>　　　　　　　　　｜<br>　　　　　　　　　C* | (E + Z)-2-PROPYL-2-NONENAL |
| C—C—C—C—C=C—C—C—C<br>　　｜　　　｜<br>　　C　　　C* | (E + Z)-2-PROPYL-7-METHYL-2-OCTENAL |
| C—C—C—C—C=C—C—C—C<br>　　　｜　　｜<br>　　　C　　C* | (E + Z)-2-PROPYL-5-METHYL-2-OCTENAL |
| 　　　　　　C<br>　　　　　　｜<br>C—C—C—C—C=C—C—C—C<br>　　　　　　｜<br>　　　　　　C* | (E + Z)-2-(1-METHYLBUTYL)-2-HEPTENAL |
| C—C—C—C—C=C—C—C—C—C<br>　　　　　｜　　｜<br>　　　　　C*　C | (E + Z)-2-(3-METHYLBUTYL)-2-HEPTENAL |
| C—C—C—C—C=C—C—C—C—C<br>　　　　　　｜<br>　　　　　　C* | (E + Z)-2-PENTYL-2-HEPTENAL |
| 　　　　　　C<br>　　　　　　｜<br>C—C—C—C—C=C—C—C—C<br>　　　　　｜　　｜<br>　　　　　C*　C | (E + Z)-2-(1,2-DIMETHYLPROPYL)-2-HEPTENAL |

TABLE 7-continued
2-DECENALS AND 2-DODECENALS FROM ALDOL OF PENTANAL AND DIMATE HEXENES HEPTANALS

| STRUCTURE | COMPOUND NAME |
|---|---|
| ```
      C
      |
C—C—C—C—C=C—C—C—C
|         |
C         C*
``` | (E + Z)-2-PROPYL-4,5-DIMETHYL-2-HEPTENAL |
| ```
C—C—C—C—C—C=C—C—C—C
          |     |
          C     C*
``` | (E + Z)-2-PROPYL-4-METHYL-2-OCTENAL |
| ```
C—C—C—C—C=C—C—C—C
        |     |
      C—C     C*
``` | (E + Z)-2-PROPYL-4-ETHYL-2-OCTENAL |

The structure of most of the product is represented by the following formula:

Structure of $C_{10}$ to $C_{14}$ Enals from Aldol of Pentanal with heptanals from Oxo of Dimate Hexenes.

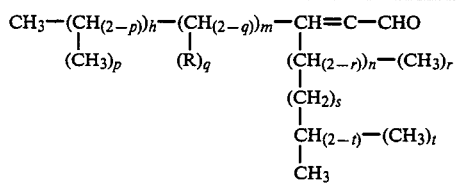

Wherein:
R=methyl or ethyl; h and m=0, 1, 3, 4 and 5;
h and s=0, 1, 2; p, q, r and t=0 or 1;
m+h can never=more than 5
q and p=0 when m+h=5 or when m+h=3
h=3 and m=1 when R=methyl and q=1 and p=0;
q=0 and p=1 when h=2 and m=2 or when h=1 and m=3;
n+s can never=more than 3
r and t=0 when n+s=3 or when n+s=1;
s=0 when n, r and t=1 or when n=2 and r=0 and t=1;
s=1 when n=1 and t and r=0 or 1 but only one of t and r can be 1; s=2 when t=1 and n=0;
h=2 and m=1 when R=ethyl and q=1 and p=0

EXAMPLE 20

The autoclave of Example 1 was charged with 0.25 g carbonylbis (triphenylphosphine) rhodium (I) chloride, 11.78 g triphenylphosphine, 46.20 g 3-methylbutene-1 and 300 psi (2068.4 KPa) gauge 1:1 CO and $H_2$. The autoclave was heated to 130° C. and held at this temperature for one hour and 35 minutes. The autoclave was cooled and the product removed under a blanket of argon and analyzed. The product is 83% 4-methylpentanal with 7% 3-methylpentanal and 7% unreacted 3-methylbutene-1 starting material.

EXAMPLE 21

Hydroformylation was carried out on 2-methylbutene-1 with rhodium catalyst in accord with the procedure of Exammple 20 at 100° C. for an eight hour fifteen minute period. A 49% conversion was obtained with 98% selectivity to 3-methylpentanal.

EXAMPLE 22

An aldehyde mixture representative of that from the oxo reactions as described above in Examples 20 and 21 was reacted in an aldol condensation. An autoclave was charged with 50 ml 0.8M NaOH, 50 ml methanol, and 10 psig (68.9 KPa) argon. The autoclave was heated to 100° C. with agitation set at 1500 rpm and the mixture of 23.08 g 3-methylpentanal and 23.11 g 4-methylpentanal, 50 ml total, were pressured into the autoclave with argon. The reaction was run for an additional hour and the system rapidly cooled. The product was removed and the upper and lower phases were separated. The upper phase contained 2% methanol, 4.0% unreacted 3-methylpentanal, 2.6% unreacted 4-methylpentanal, 0.4% hexanols, 0.6% high boilers with 92.4% as dodecenals. The skeletal structures of the dodecenals are the same as the first four structures of dodecenals listed in Table 8 which details skeletal structures of a mixed pentene stream with Dimate ® hexenes, if hydroformylated with cobalt catalyst and aldol condensed as in Examples 17 and 18.

TABLE 8
2-DODECENALS AND 2-TRIDECENALS FROM OXO AND ALDOL OF PENTENES AND DIMATE ® HEXENES

| STRUCTURE | COMPOUND NAME |
|---|---|
| ```
C—C—C—C—C=C—C—C—C
    |     |   |
    C     C*  C
``` | (E + Z)-2-(2-METHYLPROPYL)-6-METHYL-2-HEPTENAL |
| ```
C—C—C—C—C=C—C—C—C
      |     |   |
      C     C*  C
``` | (E + Z)-2-(2-METHYLPROPYL)-5-METHYL-2-HEPTENAL |

TABLE 8-continued

2-DODECENALS AND 2-TRIDECENALS FROM OXO AND ALDOL OF PENTENES AND DIMATE ® HEXENES

| STRUCTURE | COMPOUND NAME |
|---|---|
| C—C—C—C=C—C(C)—C—C with C branch | (E + Z)-2-(1-METHYLPROPYL)-6-METHYL-2-HEPTENAL |
| C—C—C—C=C(C)—C*—C—C with C branch | (E + Z)-2-(1-METHYLPROPYL)-5-METHYL-2-HEPTENAL |
| C—C—C—C—C—C=C(C*)—C—C—C | (E + Z)-2-BUTYL-2-OCTENAL |
| C—C—C—C=C(C*)—C—C—C—C with C branch | (E + Z)-2-BUTYL-6-METHYL-2-HEPTENAL |
| C—C—C—C=C(C*)—C—C—C—C with C branch | (E + Z)-2-BUTYL-5-METHYL-2-HEPTENAL |
| C—C(C)—C—C=C(C*)—C—C—C—C with C branch | (E + Z)-2-BUTYL-4,5-DIMETHYL-2-HEXENAL |
| C—C—C—C—C—C=C(C)—C*—C—C | (E + Z)-2-(1-METHYLPROPYL)-2-OCTENAL |
| C—C—C—C—C—C=C(C*)—C(C)—C | (E + Z)-2-(2-METHYLPROPYL)-2-OCTENAL |
| C—C(C)—C—C=C(C*)—C(C)—C—C | (E + Z)-2-(1-METHYLPROPYL)-4,5-DIMETHYL-2-HEXENAL |
| C—C—C—C=C(C*)—C(C)—C—C—C | (E + Z)-2-BUTYL-4-METHYL-2-HEPTENAL |
| C—C—C—C=C(C*)—C—C—C with C—C branch | (E + Z)-2-BUTYL-4-ETHYL-2-HEPTENAL |
| C—C—C(C)—C=C(C)—C—C—C—C | (E + Z)-2-BUTYL-4,5-DIMETHYL-2-HEXENAL |
| C—C—C—C—C—C=C(C*)—C—C—C—C | (E + Z)-2-BUTYL-2-NONENAL |
| C—C—C—C—C=C(C*)—C—C—C—C | (E + Z)-2-PENTYL-2-HEPTENAL |
| C—C—C—C—C—C=C(C*)—C(C)—C—C | (E + Z)-2-(2-METHYLPROPYL)-2-NONENAL |
| C—C—C—C=C(C*)—C—C—C—C with C branch | (E + Z)-2-PENTYL-4-METHYL-2-HEPTENAL |

TABLE 8-continued

2-DODECENALS AND 2-TRIDECENALS FROM OXO AND ALDOL OF PENTENES AND DIMATE ® HEXENES

| STRUCTURE | COMPOUND NAME |
|---|---|
| C—C—C—C=C—C—C—C—C<br>　　|　　|<br>　　C　　C* | (E + Z)-2-PENTYL-5-METHYL-2-HEPTENAL |
| C—C—C—C=C—C—C—C—C<br>　|　　　|<br>　C　　　C* | (E + Z)-2-PENTYL-6-METHYL-2-HEPTENAL |
| C—C—C—C—C=C—C—C—C—C<br>　　|　　　　|<br>　　C　　　　C* | (E + Z)-2-BUTYL-7-METHYL-2-OCTENAL |
| 　　C<br>　　|<br>C—C—C—C=C—C—C—C—C<br>　|　　　　|<br>　C　　　　C* | (E + Z)-2-BUTYL-5,6-DIMETHYL-2-HEPTENAL |
| 　　C<br>　　|<br>C—C—C—C=C—C—C—C—C—C<br>　|　　　|<br>　C　　　C* | (E + Z)-2-PENTYL-4,5-DIMETHYL-2-HEXENAL |
| 　　　　　　　　C<br>　　　　　　　　|<br>C—C—C—C—C—C=C—C—C—C<br>　　　　　　　　　|<br>　　　　　　　　　C* | (E + Z)-2-(1-METHYLPROPYL)-2-NONENAL |
| 　　　　　　　　C<br>　　　　　　　　|<br>C—C—C—C—C=C—C—C—C<br>　　　　　　　|　|<br>　　　　　　　C* C | (E + Z)-2-(1,2-DIMETHYLPROPYL)-2-OCTENAL |
| C—C—C—C=C—C—C—C—C<br>　　|　　　|<br>　C—C　　C* | (E + Z)-2-BUTYL-4-ETHYL-2-HEPTENAL |
| C—C—C—C=C—C—C—C—C<br>　|　　　|<br>　C—C　C* | (E + Z)-2-PENTYL-4-ETHYL-2-HEXENAL |
| C—C—C—C=C—C—C—C<br>　|　　　|　　|<br>　C　　C*　C | (E + Z)-2-(2-METHYLPROPYL)-6-METHYL-2-HEPTENAL |
| 　　C<br>　　|<br>C—C—C—C=C—C—C—C<br>　|　　　|　　|<br>　C　　C*　C | (E + Z)-2-(2-METHYLPROPYL)-4,5-DIMETHYL-2-HEXENAL |
| C—C—C—C—C=C—C—C—C<br>　　　|　　|　|<br>　　　C　C* C | (E + Z)-2-(2-METHYLPROPYL)-5-METHYL-2-OCTENAL |
| 　　　　　　　　C<br>　　　　　　　　|<br>C—C—C—C—C=C—C—C—C<br>　　　　　|　　|<br>　　　　　C　C* | (E + Z)-2-(1-METHYLBUTYL)-5-METHYL-2-HEPTENAL |
| C—C—C—C=C—C—C—C—C<br>　|　　　|　　|<br>　C　　C*　C | (E + Z)-2-(3-METHYLBUTYL)-6-METHYL-2-HEPTENAL |
| 　　C<br>　　|<br>C—C—C—C=C—C—C—C<br>　|　　　|　　|<br>　C　　C*　C | (E + Z)-2-(3-METHYLBUTYL)-4,5-DIMETHYL-2-HEPTENAL |
| 　　C　　　　C<br>　　|　　　　|<br>C—C—C—C=C—C—C—C<br>　|　　　|<br>　C　　C* | (E + Z)-2-(1-METHYLPROPYL)-4,5-DIMETHYL-2-HEPTENAL |

TABLE 8-continued
2-DODECENALS AND 2-TRIDECENALS FROM OXO AND ALDOL OF PENTENES AND DIMATE ® HEXENES

| STRUCTURE | COMPOUND NAME |
|---|---|
| C—C—C—C—C—C=C—C—C—C with C branch on C1 and C,C* branches on C7 | (E + Z)-2-(1-METHYLPROPYL)-7-METHYL-2-OCTENAL |
| C—C—C—C—C=C—C—C—C—C with C branch on C1 and C,C* branches on C6 | (E + Z)-2-(1-METHYLBUTYL)-6-METHYL-2-HEPTENAL |
| C—C—C—C—C=C—C—C—C—C with C, C* and C branches | (E + Z)-2-(3-METHYLBUTYL)-4-METHYL-2-HEPTENAL |
| C—C—C—C=C—C—C—C with C—C and C* branches and C branch | (E + Z)-2-(1-METHYLBUTYL)-4-ETHYL-2-HEXENAL |
| C—C—C—C—C=C—C—C with C—C, C* and C branches | (E + Z)-2-(1-METHYLPROPYL)-4-ETHYL-2-HEPTENAL |
| C—C—C—C—C=C—C—C—C with C, C* and C branches | (E + Z)-2-(1-METHYLBUTYL)-4-METHYL-2-HEPTENAL |
| C—C—C—C=C—C—C—C with C—C, C* and C branches | (E + Z)-2-(3-METHYLBUTYL)-4-ETHYL-2-HEXENAL |
| C—C—C—C—C=C—C—C—C with C—C, C* and C branches | (E + Z)-2-(2-METHYLPROPYL)-4-ETHYL-2-HEPTENAL |
| C—C—C—C—C=C—C—C—C with C, C* and C branches | (E + Z)-2-(1,2-DIMETHYLPROPYL)-7-METHYL-2-HEXENAL |
| C—C—C—C—C=C—C—C—C with C, C* and C branches | (E + Z)-2-(1,2-DIMETHYLPROPYL)-5-METHYL-2-HEXENAL |
| C—C—C—C—C=C—C—C—C with C, C* and C branches | (E + Z)-2-(1,2-DIMETHYLPROPYL)-4-METHYL-2-HEPTENAL |
| C—C—C—C=C—C—C—C with C—C, C* and C branches and C branch | (E + Z)-2-(1,2-DIMETHYLPROPYL)-2-ETHYL-2-HEXENAL |
| C—C—C—C—C=C—C—C—C—C with C and C*, C branches | (E + Z)-2-(2-METHYLPROPYL)-6-METHYL-2-OCTENAL |
| C—C—C—C—C=C—C—C—C—C with C and C* branches | (E + Z)-2-(1-METHYLBUTYL)-4,6-DIMETHYL-2-HEPTENAL |
| C—C—C—C—C=C—C—C—C with C, C* and C branches | (E + Z)-2-(1,2-DIMETHYLPROPYL)-5-METHYL-2-HEPTENAL |

TABLE 8-continued

2-DODECENALS AND 2-TRIDECENALS FROM OXO AND ALDOL OF PENTENES AND DIMATE ® HEXENES

| STRUCTURE | COMPOUND NAME |
|---|---|
| C—C—C—C—C—C=C—C—C—C—C<br>                                 C*     C | (E + Z)-2-(3-METHYLBUTYL)-2-OCTENAL |
| C—C—C—C—C=C—C—C—C—C<br>            C         C* | (E + Z)-2-BUTYL-5-METHYL-2-OCTENAL |
|                             C<br>C—C—C—C—C=C—C—C—C<br>                         C* | (E + Z)-2-(1-METHYLBUTYL)-2-OCTENAL |
| C—C—C—C=C—C—C—C—C<br>          C        C*        C | (E + 2)-2-(3-METHYLBUTYL)-5-METHYL-HEPTENAL |
|                        C<br>C—C—C—C=C—C—C—C<br>     C       C*    C | (E + Z)-2-(1,2-DIMETHYLPROPYL)-6-METHYL-2-HEPTENAL |
|     C             C<br>C—C—C—C=C—C—C—C<br>     C         C | (E + Z)-2-(1-METHYLBUTYL)-4,5-DIMETHYL-2-HEXENAL |
|     C            C<br>C—C—C=C—C—C—C<br>     C        C    C* | (E + Z)-2-(1,2-DIMETHYLPROPYL)-4,5-DIMETHYL-2-HEXENAL |
|                             C<br>C—C—C—C—C=C—C—C—C<br>                        C       C* | (E + Z)-2-(2-METHYLPROPYL)-4-METHYL-2-OCTENAL |
|                           C<br>C—C—C—C—C=C—C—C—C<br>                    C       C* | (E + Z)-2-(1-METHYLPROPYL)-4-METHYL-2-OCTENAL |
| C—C—C—C—C=C—C—C—C<br>                    C       C* | (E + Z)-2-BUTYL-4-METHYL-2-OCTENAL |
|                     C<br>C—C—C—C=C—C—C—C<br> C—C       C*   C | (E + Z)-2-(1,2-DIMETHYLPROPYL)-4-ETHYL-2-OCTENAL |
| C—C—C—C—C=C—C—C—C<br>                  C*   C | (E + Z)-2-(2-METHYLPROPYL)-2-OCTENAL |
|     C<br>C—C—C=C—C—C—C—C<br>    C        C* | (E + Z)-2-BUTYL-4,5-DIMETHYL-2-HEXENAL |
|                        C<br>C—C—C—C—C=C—C—C—C<br>                    C* | (E + Z)-2-(1-METHYLPROPYL)-2-OCTENAL |

Similarly, such oxo-aldol reactions of a predominant component of isoamylene streams, 2-methyl-butene-2, would produce an enal mixture with most components represented by the structure:

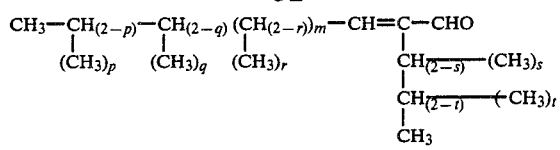

Wherein:

m=0 or 1
p, q, r, s, t=0 or 1 but only one of s and t can be 1;
m=1 when r=o and only one of p and q can be 1;
m=0 when p and q=1

At the oxo stage of the reaction the main aldehydes produced are 3-methylpentanal-1 and 4-methylpentanal-1 with possibly up to 10% 2,3-dimethylbutanal-1. The aldol products are mainly 5-methyl-2-(1-methylpropyl)hept-2-enal-1,6-methyl-2-(2-methylpropyl)-hept-2-enal-1,6-methyl-2(1-methylpropyl)hept-2-enal-1 and 5-methyl-2 (2-methylpropylhept-2-enal-1, and two $C_{10}$ aldehydes in very small amounts.

EXAMPLE 23

The unsaturated aldehydes representative of product from oxo and aldol reactions of 2-methylbutene-1 and 3-methylbutene-1 as produced in Example 22 were subjected to hydrogenation. An autoclave was charged with 3.74 g of 45%+5% cobalt on Kieselghur, 37.27 g of the aldol condensation product, 23.16 g methanol and hydrogen to 1500 psi (10,644 KPa) gauge. The autoclave was heated to 160° C. The pressure and temperature were maintained for seventeen hours. The catalyst was filtered off and washed with methanol to remove any residual alcohols. The dodecanols were distilled at 25 mm Hg and collected from 137° to 139° C.

EXAMPLE 24

This example illustrates the utility of the invention for synthesis of $C_{11}$ and $C_{14}$ unsaturated aldehydes.

An aldehyde mixture representative of that from the oxo reaction of Dimate ® hexenes, as described above in Example 1 was reacted in an aldol condensation along with normal butanal. A stirred autoclave was charged with 600 ml 0.8M NaOH, 1160 ml methanol and 20 psig (137.8 KPa) argon. The autoclave was heated to 100° C. and a mixture of 323.2 g heptanals from oxo of Dimate ® hexenes and 212.9 g butanal, total volume 600 ml was pressured into the autoclave with argon. The reaction was run for an additional hour and the system rapidly cooled. The product was removed and the upper and lower phases were separated. The upper phase contained 2.7% methanol, 5.1% unreacted heptanals, 13.7% (Z+E)-2-ethyl-hexenal, 56.0% 2-undecenals, 18.4% 2-tetradecenals, 0.5% heptanols and 3.5% high boilers. The mole ratio of the butanal to heptanals is 1.04:1, the mole ratio of the product aldehydes, 2-ethyl-hexenal, 2-undecenals and 2-tetradecenals is 0.84 to 2.51 to 0.65 respectively. The 2-undecenals were separated from the other products by reduced pressure distillation at 40 mm Hg. The 2-undecenals were collected in the temperature range of 119° to 132° C. The skeletal structures of the undecenals are given in Table 9.

TABLE 9

| 2-UNDECENALS FROM ALDOL OF HEPTANALS AND BUTANAL | |
|---|---|
| STRUCTURE | COMPOUND NAME |
| C—C—C—C—C—C—C=C—C—C<br>　　　　　　　　　　　　　│<br>　　　　　　　　　　　　　C* | (E + Z)-2-ETHYL-2-NONENAL |
| C—C—C—C—C=C—C—C<br>　　　│　　　　　　│<br>　　　C　　　　　　C* | (E + Z)-2-ETHYL-7-METHYL-2-OCTENAL |
| C—C—C—C—C—C=C—C—C<br>　　　　　│　　　　　│<br>　　　　　C　　　　　C* | (E + Z)-2-ETHYL-5-METHYL-2-OCTENAL |
| 　　　　　　　C<br>　　　　　　　│<br>C—C—C—C=C—C—C—C<br>　　　　　　　│<br>　　　　　　　C* | (E + Z)-2-(1-METHYLBUTYL)-2-HEXENAL |
| C—C—C—C=C—C—C—C—C<br>　　　　　　　│　　　│<br>　　　　　　　C*　　C | (E + Z)-2-(3-METHYLBUTYL)-2-HEXENAL |
| C—C—C—C=C—C—C—C—C<br>　　　　　　　│<br>　　　　　　　C* | (E + Z)-2-PENTYL-2-HEXENAL |
| 　　　　　　　C<br>　　　　　　　│<br>C—C—C—C=C—C—C—C<br>　　　　　　　│　│<br>　　　　　　　C* C | (E + Z)-2-(1,2-DIMETHYLPROPYL)-2-HEXENAL |
| 　　　C<br>　　　│<br>C—C—C—C—C=C—C—C<br>　　　│　　　　　│<br>　　　C　　　　　C* | (E + Z)-2-ETHYL-4,5-DIMETHYL-2-HEPTENAL |

TABLE 9-continued

2-UNDECENALS FROM ALDOL OF HEPTANALS AND BUTANAL

| STRUCTURE | COMPOUND NAME |
|---|---|
| C—C—C—C—C—C=C—C—C<br>      \|         \|<br>      C        C* | (E + Z)-2-ETHYL-4-METHYL-2-OCTENAL |
| C—C—C—C—C=C—C—C<br>    \|          \|<br>    C—C       C* | (E + Z)-2-ETHYL-4-ETHYL-2-HEPTENAL |

The 2-undecenals and 2-tetradecenals in the product which are suitable for preparing detergent hydrophobes, can be represented by the following formula:

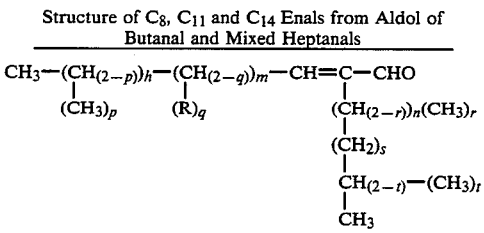

Structure of $C_8$, $C_{11}$ and $C_{14}$ Enals from Aldol of Butanal and Mixed Heptanals Wherein:
R=methyl of ethyl; m and n=0, 1, 2, 3, 4, and 5;
n and s=0, 1, 2; p, q, r and t=0 or 1;
q and p=0 when $m+h=5$ or when $m+h=2$;
n+s can never be greater than 2;
m+h can never be greater than 5;
h=3 and m=1 when R=methyl and q=1 and p=0;
h=2 and m=1 when R=ethyl and q=1 and p=0 or when q=0 and p=1;
h=1 and m=3 when p=1 and q=0;
r and t=0 when $n+s=3$ or when $n+s=0$;
s=0 when n, r and t=1 or when n=2, r=0 and t=1;
s=1 when n=1 and t and r=0 or 1 but only one of t and r can be 1;
s=2 when t=1 and n=0.

EXAMPLE 25

This example illustrates the utility of the invention for a single hexene isomer, 4-methylpentene-1. The hydroformylation was performed in a 300 ml autoclave with agitation. The autoclave was charged with 0.29 g carbonyltris(triphenylphosphine)rhodium hydride, 33.0 g triphenylphosphine, 100.0 g 4-methylpentene-1 and 200 psi (200 KPa) gauge pressure with 9 parts hydrogen to 1 part CO. The autoclave was heated to 100° C. and the pressure brought to 300 psi (2068.4 KPa) gauge using feed gas in 1 to 1 ratio hydrogen to CO. The temperature and pressure were maintained for 2 hours and 45 minutes after which the autoclave and contents were cooled rapidly. The product was removed and analyzed chromatographically. The product consists of 5.65% hexenes (5.57% 4-methylpentene-1), 10.64% 2,4-dimethylpentanal, 68.84% 5-methylhexanal, and approx. 15% triphenylphosphine, by area percent.

An aldehyde mixture representative of the oxo reaction of 4-methylpentene-1, as described above was reacted in an aldol condensation. The reaction vessel was a 100 ml 3 neck round bottom flask equipped with pressure equilizing funnel, thermometer, spiral condensor, a mechanical stirrer and a nitrogen blanket, maintained by using a slow bleed of nitrogen and a mineral oil bubbler. The reactor was charged with 12 ml 0.8 M NaOH, and 12 ml 2,5-hexanediol, as co-solvent. The system was heated to 80° C. and the aldehydes, 12 ml, were added over a six minute period. The system was heated to 89°–90° C. and held at temperature for an additional 30 minutes. The system was cooled and the upper and lower phases were separated. The upper phase was analyzed chromatographically and contained 2.0% 2,4-dimethylpentanal, 1.5% 5-methylhexanal, 5% tetradecenal isomers, 85% 7-methyl-2-(3-methylbutyl)-2-octenal, 2.5% 2,5-hexanediol and a balance of high boilers.

EXAMPLE 26

The unsaturated aldehydes representative of product from oxo and aldol reactions of 4 methylpentene-1 as in example 25 were subject to hydrogenation. The reaction was performed in a 300 ml autoclave which was charged with 0.90 g 45+5% cobalt on Kieselghur, 7.92 g unsaturated aldehydes, 50.02 g methanol (used to ensure proper mixing) and 1500 psi (10644 KPa) gauge hydrogen. The autoclave was heated to 150° C. The pressure and temperature were maintained for one hour. The catalyst was filtered off and washed with methanol to remove any residual alcohols. The 7-methyl-2-(3-methylbuty)-2-octenal was distilled at 20 mm Hg and was collected from 158° to 159° C. This example combined with Example 28 illustrates the conversion of the unsaturated aldehydes to saturated carboxylic acids.

EXAMPLE 27

Hydrogenation to a saturated aldehyde from an unsaturated aldehyde mixture representative of that from the oxo and aldol of Dimate ® hexenes as described in Examples 1 and 17, was carried out in a 300 ml autoclave with agitation. The autoclave was charged with 2.60 g 5% palladium on carbon, 44.81 g methanol (used to ensure proper agitation), 8.24 g tetrade-2-enals and 200 psig (1379 KPa) $H_2$. The autoclave was heated to 85° C. and held for one hour. The autoclave was then heated to 125° C. and held for 2 hours. The autoclave was cooled and an infrared spectrometric analysis confirmed the reduction of the olefinic bond and the presence of a strong carbonyl band at 1740 cm$^{-1}$. The untreated 2-tetradecenals have bands at 1698 cm$^{-1}$, strong, and 1643 cm$^{-1}$ moderate, which are characteristic of unsaturated aldehydes.

EXAMPLE 28

This example, combined with Example 27 illustrates the conversion of the unsaturated aldehydes to saturated carboxylic acids.

Oxidation of a saturated aldehyde mixture representative of that from the hydrogenation of the unsaturated aldehydes as described in Example 27 was carried out in a Fisher-Porter aerosol bomb, with agitation. The bomb was charged with 60 ml heptene, 8.2 g tetradecanals, and 100 psi (689,4 KPa) gauge oxygen. Agitation was started and pressure was allowed to drop to 60 psi (413.7 KPa) gauge when the bomb would be re-pressured to 100 psi gauge. The reaction continued for 3¼ hours and the temperature varied from 23° to 30° C. The pressure was released and system heated to 80° C. and held for 2 hours. The product was analyzed chromatographically and by gas liquid chromatography - mass spectrometry to confirm that saturated acid was formed, and 98% of the aldehydes were converted.

EXAMPLE 29

Oxidation of an unsaturated aldehyde mixture representative of that from the oxo and aldol reactions described in Examples 1 and 17, was carried out in a Fisher-Porter aerosol bomb with agitation. The bomb was charged with 60 ml heptane, 8.2 g tetradec-2-enal and 100 psi (689.4 KPa) gauge oxygen in a darkened area. Agitation was started and the pressure in the bomb was allowed to drop to 70 psi (482.63 KPa) gauge at which time the bomb was repressurized to 100 psi (689.4 KPa) gauge. The reaction continued in this manner for four hours and the temperature varied from 20° C. to 25° C. The pressure was released and the system heated to 80° C. for 2 hours. The product was analyzed chromatographically and by mass spectrometry and contained unsaturated tetradecanoic acids and 97% of the aldehydes were converted.

A mixture of amylenes and Dimate ® hexenes can be subjected to oxo and aldol processes in accord with the present invention. Thus, pentenes containing n-pentene-1, n-pentene-2, 3-methylbutene-1, 2-methylbutene-2, and 2-methylbutene-1 in admixture with Dimate ® hexenes can be reacted in an oxo reaction, with the product treated in an aldol reaction, in accord with procedures in Examples 18 and 19, and the resulting enals (see Table 8) can be represented by the following structure:

Structure of Dodec-2-enals and Tridec-2-enals
from the, Oxo-Aldol of mixed pentenes
and Dimate Hexenes

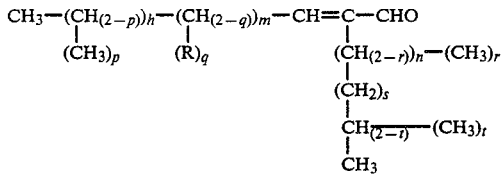

Wherein:
R=methyl or ethyl; h and m=0, 1, 2, 3, 4 and 5;
n and s=0, 1, 2; p, q, r and t=—0, 1;
m+h=5 or 4, when p and q=0;
m and q=1 and p=0 when h=3, 2 or 1 but R can only be ethyl when h=1, 2 and R can only be methyl when h=2, 3;
h+m can never be greater than 5;
n+s can never be greater than 2;
q=0 and p=1 and h=1 when m=3 or 2;
r and t=0 when n+s=3 or when n=0 and s=2;
t=1 when n=0 or 1 and s=1 or 2;
n and t=1 when s=0 and r=1;

The aldehydes which are branched at the 2-position which react at a much slower rate in the aldol reaction can be recycled to generate $C_{11}$-$C_{16}$ enals in several different ways. Thus these aldehydes can be simply recycled to the aldol reaction until their concentration is high enough that they are being reacted in cross-aldol reactions at a rate essentially the same as they are being generated in the hydroformylation reaction. Another approach is to allow these relatively unreactive aldehydes to proceed through hydrogenation to give branched chain alcohols. These alcohols can then be readily dehydrated to a mixture of branched olefins. If these olefins are recycled to the hydroformylation reaction they are hydroformylated primarily to aldehydes *without* a branch at the 2-position and hence they will undergo the alcohol reaction and generate aldol products in the desired $C_{11}$ to $C_{16}$ range. This can be illustrated by considering the mixture of aldehydes generated by the hydroformylation of Dimate ® hexenes (see Table 2). The 2-methylhexanal, 2-ethylpentanal and 2,4-dimethylpentanal isomers pass through the aldol reaction stage largely unreacted. On hydrogenation they are converted to 2-methylhexanol, 2-ethylpentanol and 2,4-dimethylpentanol. These alcohols can be dehydrated by passage over heterogeneous catalysts at temperatures of 120°-500° C. Catalysts should be chosen such that alcohol dehydration occurs readily but minimal skeletal rearrangement occurs. Suitable catalysts are various types of aluminas, thorias and metal phosphates (e.g. $AlPO_4$, $BPO_4$, $Ca_3(PO_4)_2$. (For further catalyst information see Journal of the American chemical Society, 85, 2180 (1963) and Topics in Phosphorus Chemistry Vol. 10. page 285). As an example we can consider the recycle of 2-methylhexano. Over a dehydration catalyst it would give primarily 2-methylhexene-1 and 2-methylhexene 2. These olefins when charged to the hydroformylation reaction would give rise to primarily 3-methylheptanal with lesser amounts of 6-methylheptanal and minor amounts of other isomers. The 3-methylheptanal and 6-methylheptanal readily undergo aldol condensation and in conjunction with the $C_7$ aldehydes resulting directly from the hydroformylation of the Dimate R hexenes will give rise to predominantly $C_{15}$ unsaturated aldehydes with minor amounts of $C_{16}$ unsaturated aldehydes. See Table 10 for specific names of the unsaturated aldehyde products. The described recycle involving dehydration and formation of aldolable aldehydes, permits handling smaller volumes of materials in the aldol reaction than is the case when the concentration of 2-branched aldehyde reactant is permitted to build up.

TABLE 10

2-PENTADECENALS AND 2-HEXADECENALS FROM OXO AND ALDOL OF DIMATE ® HEXENES AND RECYCLED UNREACTIVE HEPTANALS

| COMPOUND NAME |
| --- |
| (E + Z)-2-(1-METHYLPENTYL)-2-NONENAL |
| (E + Z)-2-(1-METHYLPENTYL)-7-METHYL-2-OCTENAL |
| (E + Z)-2-(1-METHYLPENTYL)-5-METHYL-2-OCTENAL |
| (E + Z)-2-(1-METHYLPENTYL)-5,6-DIMETHYL-2-HEPTENAL |
| (E + Z)-2-PENTYL-5-METHYL-2-NONENAL |
| (E + Z)-2-(1-METHYLBUTYL)-5-METHYL-2-NONENAL |
| (E + Z)-2-(3-METHYLBUTYL)-5-METHYL-2-NONENAL |
| (E + Z)-2-(1,2-DIMETHYLPROPYL)-5-METHYL-2-NONENAL |
| (E + Z)-2-(1-METHYLPENTYL)-4-METHYL-2-OCTENAL |
| (E + Z)-2-(1-METHYLPENTYL)4-ETHYL-2-HEPTENAL |
| (E + Z)-2-(4-METHYLPENTYL)-2-NONENAL |
| (E + Z)-2-(4-METHYLPENTYL)-7-METHYL-2-OCTENAL |
| (E + -2-(4-METHYLPENTYL)-5-METHYL-2-OCTENAL |
| (E + Z)-2-(4-METHYLPENTYL)-5,6-DIMETHYL-2-HEPTENAL |
| (E + Z)-2-PENTYL-8-METHYL-2-NONENAL |
| (E + Z)-2-(1-METHYLBUTYL)-8-METHYL-2-NONENAL |

TABLE 10-continued
2-PENTADECENALS AND 2-HEXADECENALS FROM OXO AND ALDOL OF DIMATE ® HEXENES AND RECYCLED UNREACTIVE HEPTANALS (E + Z)-2-(3-METHYLBUTYL)-8-METHYL-2-NONENAL
(E + Z)-2-(1,2-DIMETHYLPROPYL)-
8-METHYL-2-NONENAL
(E + Z)-2-(4-METHYLPENTYL)-4-METHYL-2-OCTENAL
(E + Z)-2-(4-METHYLPENTYL)4-
ETHYL-2-HEPTENAL
(E + Z)-2-(1-ETHYLBUTYL)-2-NONENAL
(E + Z)-2-(1-ETHYLBUTYL)-7-METHYL-2-OCTENAL
(E + Z)-2-(1-ETHYLBUTYL)-5-METHYL-2-OCTENAL
(E + Z)-2-(1-ETHYLBUTYL)-
5,6-DIMETHYL-2-HEPTENAL
(E + Z)-2-PENTYL-5-ETHYL-2-OCTENAL
(E + Z)-2-(1-METHYLBUTYL)-
5-ETHYL-2-OCTENAL
(E + Z)-2-(3-METHYLBUTYL)-
5-ETHYL-2-OCTENAL
(E + Z)-2-(1,2-DIMETHYLPROPYL)-
5-ETHYL-2-OCTENAL
(E + Z)-2-(1-ETHYLBUTYL)-4-METHYL-2-OCTENAL
(E + Z)-2-(1-ETHYLBUTYL)-4-ETHYL-2-HEPTENAL
(E + Z)-2-PENTYL-4-ETHYL-
6-METHYL-2-HEPTENAL
(E + Z)-2-(1-METHYLBUTYL)-4-
ETHYL-6-METHYL-2-HEPTENAL
(E + Z)-2-(3-METHYLBUTYL)-4-
ETHYL-6-METHYL-2-HEPTENAL
(E + Z)-2-(1,2-DIMETHYLPROPYL)-
4-ETHYL-6-METHYL-2-HEPTENAL
(E + Z)-2-PENTYL-4,7-DIMETHYL-2-OCTENAL
(E + Z)-2-(1-METHYLBUTYL)-4,7-
DIMETHYL-2-OCTENAL
(E + Z)-2-(3-METHYLBUTYL)-4,7-
DIMETHYL-2-OCTENAL
(E + Z)-2-(1,2-DIMETHYLPROPYL)-
4,7-DIMETHYL-2-OCTENAL
(E + Z)-2-PENTYL-4-ETHYL-
5-METHYL-2-HEXENAL
(E + Z)-2-(1-METHYLBUTYL)-4-
ETHYL-5-METHYL-2-HEXENAL
(E + Z)-2-(3-METHYLBUTYL)-4-
ETHYL-5-METHYL-2-HEXENAL
(E + Z)-2-(1,2-DIMETHYLPROPYL)-4-
ETHYL-5-METHYL-2-HEXENAL

2-HEXADECENALS (E + Z)-2-(4-METHYLPENTYL)-
7-METHYL-2-NONENAL
(E + Z)-2-(1-METHYLPENTYL)-
7-METHYL-2-NONENAL
(E + Z)-2-(1-ETHYLBUTYL)-7-
METHYL-2-NONENAL
(E + Z)-2-(4-METHYLPENTYL)-
4,7-DIMETHYL-2-OCTENAL
(E + Z)-2-(1-METHYLPENTYL)-
4,7-DIMETHYL-2-OCTENAL
(E + Z)-2-(1-ETHYLBUTYL)-
4,7-DIMETHYL-2-OCTENAL
(E + Z)-2-(4-METHYLPENTYL)-4-
ETHYL-6-METHYL-2-HEPTENAL
(E + Z)-2-(1-METHYLPENTYL)-4-
ETHYL-6-METHYL-2-HEPTENAL
(E + Z)-2-(1-ETHYLBUTYL)-4-
ETHYL-6-METHYL-2-HEPTENAL
(E + Z)-2-(4-METHYLPENTYL)-4-
ETHYL-5-METHYL-2-HEPTENAL
(E + Z)-2-(1-METHYLPENTYL)-4-
ETHYL-5-METHYL-2-HEPTENAL
(E + Z)-2-(1-ETHYLBUTYL)-4-
ETHYL-5-METHYL-2-HEPTENAL
(E + Z)-2-(4-METHYLPENTYL)-4-METHYL-2-NONENAL
(E + Z)-2-(1-METHYLPENTYL)-4-METHYL-2-NONENAL
(E + Z)-2-(1-ETHYLBUTYL)-4-METHYL-2-NONENAL
(E + Z)-2-(4-METHYLPENTYL)-4-ETHYL-2-OCTENAL
(E + Z)-2-(1-METHYLPENTYL)-4-ETHYL-2-OCTENAL
(E + Z)-2-(1-ETHYLBUTYL)-4-ETHYL-2-OCTENAL

Nonionic detergents prepared from the present alcohols by ethoxylation were tested for detersive efficiency in comparison with reference compounds which were substantially normal alcohol ethoxylates, being Neodol ® ethoxylates marketed by Shell Chemical Company. The reference compound alcohols, produced by ethylene oligomerization, are composed of designated percentages of normal alcohols, generally in the range of 70 to 80%, and the remainder of isomeric 2-alkyl (predominantly 2-methyl) primary alcohols. The tests employed are recognized tests in which a fabric soiled with synthetic sebum/airborne particulate is washed and the results measured by Rd, change in reflectance by Gardner XL-23 Color Difference meter. Tests were conducted with a polyester-cotton blend fabric containing 65% polyester, and with a cotton broadcloth fabric. Three different ethoxylates of the $C_{14}$ alcohol mixture of the present invention (designated $C_{14}$ Aldol) were used, having 6.0, 8.7 and 10.5 ethoxylate groups on the average. The reference compounds for coomparison were Neodol 45 ethoxylates having 7 and 13 ethoxyl groups, and Neodol 25 ethoxylates having 7 and 12.5 ethoxyl groups. An individual oxo-aldol $C_{14}$ alcohol of the present invention was also tested 2-(1-methylbutyl)-5-methyloctanol. It was prepared by aldol of 3-methylheptanol, and is designated as $C_{14}$ High Vicinal, because of presence of adjacent branches in its structure. The results are reported in Tables 11-a, 11-b, 11-c, 11-d, and 11-e. The tables include results with the detergent including sodium tripolyphosphate (STP) builder, sodium carbonate builder, or no builder, and a washing temperature of 120° F. in most instances, but 75° F. in Table 11-d. Tests were reported at different amounts of water hardness as set forth. The sodium tripolyphosphate built detergent, for example, had a composition of 10% of the nonionic (surfactant), 24% sodium tripolyphosphate, 12% R.U. Sebacate (as is), 53% sodium sulfate, and 1% sodium carboxyethyl cellulose, while the one with no builder was similar, with the STP replaced by additional sodium sulfate. The detergent was used in concentration 0.15%, for anionic concentration of 150 ppm. Water hardness was from a 3/2 atom ratio of calcium and magnesium ions, with concentration calculated as parts per million by weight of calcium carbonate.

TABLE 11a

Synthetic Sebum Detergency
120° F., Cotton ΔRd
30% $Na_2CO_3$ Builder System

| Sample | Water Hardness | | | |
|---|---|---|---|---|
| | 0 | 50 ppm | 100 ppm | 200 ppm |
| Neodol 45-7 | 32.5 | 31.5 | 29.6 | 27.2 |
| Neodol 45-13 | 32.3 | 31.1 | 29.2 | 23.3 |
| Neodol 25-7 | 31.8 | 29.9 | 28.8 | 23.9 |
| Neodol 25-12.5 | 33.1 | 30.7 | 27.6 | 20.2 |
| $C_{14}$ Aldol 6.0 | 32.7 | 29.4 | 26.0 | 19.8 |
| $C_{14}$ Aldol 8.7 | 32.6 | 30.8 | 27.0 | 24.0 |
| $C_{14}$ Aldol 10.5 | 31.5 | 31.1 | 28.0 | 26.2 |
| $C_{14}$ High Vicinal | | | | |
| 5.5 | 20.8 | 20.6 | 18.8 | 11.4 |
| 9.5 | 19.5 | 18.9 | 19.4 | 14.8 |
| 13.3 | 15.5 | 17.0 | 15.8 | 11.1 |

TABLE 11b

Synthetic Sebum Detergency
120° F., cotton, ΔRd
0% Builder System

| Sample | Water Hardness | | | |
|---|---|---|---|---|
| | 0 | 50 ppm | 100 ppm | 200 ppm |
| Neodol | 31.5 | 29.5 | 26.1 | 24.0 |
| Neodol | 31.4 | 31.3 | 29.5 | 27.8 |

TABLE 11b-continued

Synthetic Sebum Detergency
120° F., cotton, ΔRd
0% Builder System

| Sample | Water Hardness | | | |
|---|---|---|---|---|
| | 0 | 50 ppm | 100 ppm | 200 ppm |
| Neodol 25-7 | 31.7 | 29.4 | 26.1 | 24.8 |
| Neodol 25-12.5 | 30.1 | 31.1 | 29.7 | 25.9 |
| $C_{14}$ Aldol- 6.0 | 30.4 | 26.0 | 20.7 | 16.8 |
| $C_{14}$ Aldol- 8.7 | 30.2 | 30.6 | 24.5 | 22.4 |
| $C_{14}$ Aldol- 10.5 | 30.4 | 30.9 | 26.3 | 24.7 |
| $C_{14}$ High Vicinal | | | | |
| 5.5 | 32.7 | 18.9 | 21.0 | 13.9 |
| 9.5 | 32.1 | 20.1 | 20.3 | 17.4 |
| 13.3 | 32.6 | 17.5 | 16.1 | 14.3 |

TABLE 11c

Synthetic Sebum Detergency
120° F., Cotton, ΔRd
24% STP Builder System

| Sample | Water Hardness | | | |
|---|---|---|---|---|
| | 0 | 50 ppm | 100 ppm | 200 ppm |
| Neodol 45-7 | 32.2 | 34.2 | 35.2 | 26.9 |
| Neodol 45-13 | 31.5 | 34.0 | 35.0 | 28.9 |
| Neodol 25-7 | 32.2 | 34.4 | 34.5 | 26.1 |
| Neodol 25-12.5 | 31.7 | 33.5 | 34.5 | 27.4 |
| $C_{14}$ Aldol 6.0 | 31.4 | 34.4 | 34.5 | 20.5 |
| $C_{14}$ Aldol 8.7 | 30.8 | 33.5 | 35.7 | 23.5 |
| $C_{14}$ Aldol 10.5 | 31.4 | 34.3 | 34.8 | 25.2 |
| $C_{14}$ High Vicinal | | | | |
| 5.5 | 32.8 | 35.3 | 36.6 | 22.4 |
| 9.5 | 32.8 | 33.5 | 35.8 | 25.3 |
| 13.3 | 32.7 | 35.1 | 34.5 | 24.9 |

TABLE 11d

Synthetic Sebum Detergency
75° F., PE/cotton, ΔRd
24% STP Builder System

| Sample | Water Hardness | | | |
|---|---|---|---|---|
| | 0 | 50 ppm | 100 ppm | 200 ppm |
| Neodol 45-7 | 18.3 | 17.7 | 15.7 | 14.0 |
| Neodol 45-13 | 16.7 | 16.1 | 15.1 | 11.9 |
| Neodol 25-7 | 18.8 | 19.8 | 18.0 | 14.3 |
| Neodol 25-12.5 | 16.5 | 17.2 | 14.5 | 13.7 |
| $C_{14}$ Aldol- 6.0 | 19.8 | 17.7 | 19.3 | 9.4 |
| $C_{14}$ Aldol- 8.7 | 19.3 | 18.2 | 20.0 | 15.0 |
| $C_{14}$ Aldol- 10.5 | 17.5 | 18.1 | 16.6 | 14.0 |
| $C_{14}$ High Vicinal | | | | |
| 5.5 | 20.8 | 20.6 | 18.8 | 11.4 |
| 9.5 | 19.5 | 18.9 | 19.4 | 25.8 |
| 13.3 | 15.5 | 17.0 | 15.8 | 11.1 |

TABLE 11e

Synthetic Sebum Detergency
120° F., PE/cotton, ΔRd
24% STP Builder System

| Sample | Water Hardness | | | |
|---|---|---|---|---|
| | 0 | 50 ppm | 100 ppm | 200 ppm |
| Neodol 45-7 | 19.8 | 19.7 | 18.7 | 16.2 |
| Neodol 45-13 | 18.6 | 17.8 | 16.8 | 12.8 |
| Neodol 25-7 | 19.9 | 19.6 | 20.4 | 16.7 |
| Neodol 25-12.5 | 18.1 | 17.8 | 16.6 | 13.4 |
| $C_{14}$ Aldol 6.0 | 19.8 | 19.0 | 18.6 | 7.9 |
| $C_{14}$ Aldol 8.7 | 19.9 | 21.7 | 21.1 | 18.9 |
| $C_{14}$ Aldol 10.5 | 20.1 | 18.8 | 19.6 | 17.6 |
| $C_{14}$ High Vicinal | | | | |
| 5.5 | 21.2 | 18.9 | 21.0 | 13.9 |
| 9.5 | 20.3 | 17.4 | | |
| 73.3 | 18.4 | 17.5 | 16.1 | 14 |

It can be seen that the ethoxylates of the present alcohol mixture are in general comparable in the tests of detersive efficiency to the established reference ethoxylates. It can be noted that in some respects the present compounds give better results, as for example with the 8.7 ethoxylate in Tables 11-d and 5-e involving tests with polyester/cotton.

The $C_{14}$ mixed alcohol product of the present invention, in ethoxylate form, was tested for biodegradability, in comparison to commercial detergents. The test procedure used was the semi-continuous activated sludge test which determines dissolved organic carbon as the measure of biodegradation. The results are reported in Table 12 below. The aldol-alcohol ($C_{14}$) was the alcohol mixture as described in Table 4 above, which has been ethoxylated to have an average of 10.5 ethoxyl groups. It was compared to a Neodol 25-12, which is an ethoxylate of an approximately linear alcohol in the 12 to 15 carbon range, with an average of 12 ethoxyl groups. The two LAS reference compounds are linear alkyl benzene sulfonates of a type utilized commercially. The test-measures the removal of dissolved organic carbon (DOC), and is a measure of complete degradation of the compounds.

TABLE 12

| | Mean % DOC Removal[1] (95% Confidence Limits) | | | |
|---|---|---|---|---|
| | 2nd through 5th Week of Tests | | 6th through 8th Week of Tests | |
| Test Compound | 24-Hour Cycle (16 data points) | 72-Hour Cycle (3 data points) | 24-Hour Cycle (12 data points) | 72-Hour Cycle (3 data points) |
| Neodol 25-12 Reference Compound | 90 ± 6 | 98 ± 7 | 97 ± 2 | 100 |
| A230 LAS Reference Compound | 83 ± 7 | 92 ± 11 | 89 ± 3 | 97 ± 8 |
| Dodecen-1 Derived LAS Reference Compound | 81 ± 13 | 82 ± 59 | 89 ± 6 | 93 ± 27 |
| Aldol Alcohol ($C_{14}$) Ethoxylate (10.5 EO) | 77 ± 6 | 92 ± 16 | 88 ± 5 | 100 ± 1 |

[1]Mean % DOC Removal = (DOC in Feed − Net DOC in Effluent) × 100/DOC in Feed
Net DOC in Effluent = Test Chamber DOC − Control Chamber DOC While the degradation of the aldol product was not as fast as that of the linear alcohol product (Neodol 25-12), it was still comparable to the LAS compounds which are suitable for commercial use. Also, the essentially complete removal in the 72-hour cycles indicates there are no resistant fragments.

Further biodegradation tests were carried out utilizing the semi-continuous activated sludge test, and comparing a $C_{14}$ aldol isomeric mixture ethoxylate with an ethoxylate of a high vicinal alcohol, i.e., 3-(1-methylbutyl)-5-methylheptanol. The 24-hour cycle results for weeks 4, 5 and 6 are reported in Table 7. While the high vicinal alcohol degrades somewhat more slowly, its rate is still fairly close to that of the isomeric mixture which was shown to be comparable to commercial materials in Table 6. Moreover, results with the isomeric mixture indicate that good biodegradation can be obtained even with a substantial amount of the high vicinal alcohol present. The results in Table 7 provide a comparison of the materials tested, but may not be directly comparable to other tests, because of the low ethoxyl content which may have affected solubility, or possibly unexplained test variations.

TABLE 13

| Semi-Continuous Activated Sludge Test | | | | | | |
|---|---|---|---|---|---|---|
| | (% DOC. Removal - 24 hr) | | | | | |
| | Week 4 | | Week 5 | | Week 6 | |
| 1. Neodol ® 25-7 Reference compound | 88 | 38 | 97 | 13 | 96 | 8 |
| 2. $C_{14}$ + 6.0 Ethylene Oxide (Dimersol Hexene) | 61 | 13 | 65 | 31 | 72 | 6 |
| 3. High Vivinal Alcohol + 6.3 Ethylene Oxide (from 3-methylhexanal) | 66 | 44 | 51 | 39 | 63 | 12 |

EXAMPLE 30

The $C_{14}$ ethoxylate derivatives described above and evaluated were prepared by known ethoxylation procedures. A 100 ml glass reactor was employed with thermometer, stirrer, and provision for ethylene oxide addition. A mercury-filled U-tube manometer was employed, and about 700 mm pressure was maintained during the reaction. Ethylene oxide was charged from a small bomb, with the amount charged determined by weight difference. The weight of the detergent alcohol charge was calculated to have the desired mole ratio to ethylene oxide. The reaction temperature was maintained at 165° C. by a controlled heating mantle. As catalyst, solid KOH was charged at 1% by weight of alcohol used. Thus $C_{14}$ aldol alcohol product, like that of Table 3, was reacted in separate reactions with ethylene oxide in mole ratio of 5.3/1 and 8.9/1 EO/alcohol by weight. The ethylene oxide addition rate was controlled by a valve and required about 2 to 2.5 hours for complete addition as determined by the manometer. The temperature was reduced to 125° C. and the catalyst was neutralized by addition of $H_3PO_4$ by syringe through a rubber septum. The amount of the acid in ml of 85% $H_3PO_4$ was 0.7 times the KOH weight in grams. The product was held for 15 minutes at 125° C. following the acid addition, and was then filtered while hot through a layer of Celite ® filter aid on a fritted filter to remove phosphate salts. NMR analysis showed ethylene oxide content similar to that charged in the reactions, being 5.6 ethoxyl units and 8.7 ethoxyl units respectively. A similar procedure but with a higher EO/alcohol charge was used to prepare an ethoxylate of the same alcohol mixture, but with 10.5 ethoxyl units per alcohol molecule. The procedure was also used to prepare the $C_{14}$ high vicinal alcohol evaluated herein, using weight charges of EO/alcohol of 5.9, 8.8 and 12.1 to obtain products with 5.5, 9.5 and 13.3 ethoxyl units as shown by NMR.

EXAMPLE 31

Sulfate derivatives of the alcohols or ethoxylates were prepared by sulfation with chlorosulfonic acid. Both an alcohol mixture, and an ethoxylated alcohol mixture were sulfated in this manner. The alcohol mixture was from oxo, aldol and hydrogenation reactions starting with Dimate ® hexenes, as described hereinabove. The ethoxylate was prepared in accord with the above procedure with an ethylene oxide charge calculated to provide three ethoxylate units. The chlorosulfonic acid was provided on a 1.05 to 1 mole ratio to alcohol or ethoxylate. In separation reactions, the alcohol and ethoxylate were placed in flasks and cooled in an ice bath while acid was added dropwise. HCl vapors were then drawn off by intermittent vacuum. When HCl evolution stopped, the sulfated products were transferred to beakers containing solutions of 90% isopropanol and 10% water, by weight. The sulfate derivatives were 20% by weight of their respective solutions. A 50% by weight solution of NaOH in water was added with agitation to pH 8.0. Salts solids were removed by filtration. The solutions of sulfate derivatives were then evaporated to dryness on a rotary evaporator. The products were then in the form of a sodium sulfate of the $C_{14}$ alcohol mixture, and a sodium sulfate of the ethoxylated $C_{14}$ alcohol mixture containing a nominal 3.0 ethoxyl units. Ethanol was added to the products to form concentrated solutions, along with water to aid solubility, forming a 55.6% solution of the alcohol sulfate, and a 50.2% solution of the sulfate of the ethoxylated alcohol. The solutions are a convenient form for preparing samples for evaluation of detergency, biodegradation and similar properties. In view of the results reported herein for ethoxyl derivatives, the sulfate derivatives are expected to be similarly good.

The detergent hydrophobes of the present invention are also of interest in the form of synthetic fatty acids. The long chain aldehydes as produced herein, can readily be converted to acids by simple oxidation of the aldehyde group, as in an air oxidation. The acids retain the branched structure of the aldehyde, and can have the unsaturation at the 2-position as in the enals, or such unsaturation can be hydrogenated, or otherwise reduced, to provide saturated acids. Such acids can be converted to sodium, potassium or other alkali metal soaps or other detergents having anionic or hydrophilic groups attached to the acid, and are expected to have suitable lathering and other detergent properties. It will be noted that the acids, which can be termed as synthetic fatty acids, have the same structure as the alcohols. Since the alcohols are suitable as detergent hydrophobes, having suitable detergent and biodegradation properties, the corresponding acids are expected to have suitable detergent and biodegradation properties.

We claim:

1. A mixture of isomeric enals having from 11 to 16 carbon atoms and characterized as 2-alkenals of 6 to 10 carbon atoms with an alkyl group containing 2 to 6 carbon atoms substituted in the 2-position thereof, and with additional branching in most of the isomers with most of the additional branches being methyl groups, and further characterized as being liquid at ambient temperatures and having hydrocarbon hydrophobe moieties making the mixture suitable for formation of effective detergents therefrom, and further characterized by suitable biodegradability.

2. The mixture of claim 1 in which the aldehydes on the average have more than 2 branches in addition to the 2-branch.

3. The mixture of claim 1 in which aldehydes of different carbon numbers are present.

4. A mixture of $C_{14}$ isomemric enals which are characterized as nine-carbon 2-alkenal with a five-carbon alkyl group substituted on the 2-position thereof, and with additional branching in most of the isomers, with most of the additional branches being methyl groups, and further characterized as liquid at ambient temperature and having varying hydrocarbon hydrophobe moieties making the mixture suitable for formation of effective detergents therefrom, and further characterized by suitable biodegradability.

5. A mixture of enals in accord with claim 4 characterized by structure as set forth below:

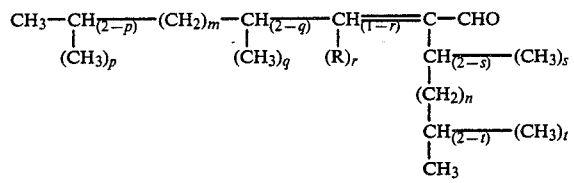

wherein:
R=methyl or ethyl;
p, q and r=0 or 1; but only one of p, q and r can be 1;
m=3, when p, q and r=0;
m=2, when r=1 and R=methyl;
m=1, when r=1 and R=ethyl;
n=2, when s and t=0;
n=1, when s or t=1;
s and t=0 or 1, but only one of s and t can be 1.

6. A mixture of enals characterized by the structure:

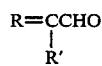

in which R is an alkylidine group with 7 carbon atoms and R' is an alkyl group with 5 carbon atoms and in which in at least about 80% of the compound, R' is selected from n-pentyl, 3-methylbutyl and 1-methylbutyl, and R is selected from n-pentyl, 3-methylbutyl and 1-methylbutyl, and R is selected from n-heptylidine, 3-methylhexylidene, 5-methylhexylidene, 2-methylhexylidene and 2-ethylpentylidene groups.

7. A mixture of isomeric enals in accord with claim 1 and further characterized as having most of the aldehydes in the mixture represented by the structure set forth below, and their saturated aldehyde, alcohol, ethoxylated alcohol, and ethoxylated alcohol surface derivatives:

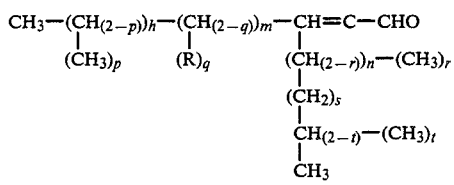

Wherein:
R=methyl or ethyl; h and m=0, 1, 3, 4 and 5;
n and s=0, 1, 2; p, q, r and t=0 or 1;
m+h can never=more than 5;
q and p=0 when $m+h=5$ or when $m+h=3$;
h=3 and m=1 when R=methyl and q=1 and p=0;

q=0 and p=1 when h=2 and m=2 or when h=1 and m=3;
n+s can never=more than 3;
r and t=0 when $n+s=3$ or when $n+s=1$;
s=0 when n, r and t=1 or when n=2 and r=0 and t=1;
s=1 when n=1 and t and r=0 or 1 but only one of t and r can be 1;
s=2 when t=1 and n=0;
h=2 and m=1 when R=ethyl and q=1 and p=0.

8. A mixture of isomeric enals in accord with claim 1 and further characterized as having most of the aldehydes in the mixture represented by the structure set forth below, and their saturated aldehyde, alcohol, ethoxylated alcohol, and ethoxylated alcohol sulfate derivates:

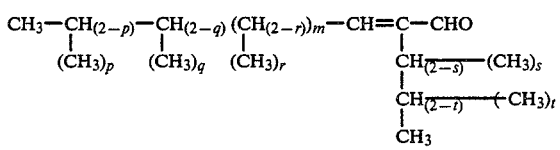

Wherein:
m=0 or 1;
p, q, r, s, t=0 or 1 but only one of s and t can be
m=1 when r=o and only one of p and q can be 1;
m=0 when p and q=1.

9. A mixture of isomeric enals in accord with claim 1 and further characterized as having most of the aldehydes in the mixture represented by the structure set forth below, and their saturated aldehyde, alcohol, ethoxylated alcohol, and ethoxylated alcohol sulfate derivatives:

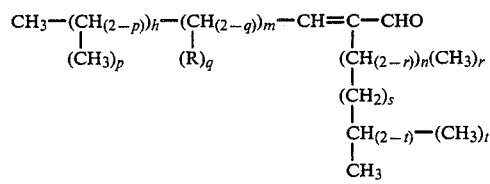

Wherein:
R=methyl or ethyl; h and m=0, 1, 2, 3, 4, and 5;
n and s=0, 1, 2; p, q, r and t=0 or 1;
q and p=0 when $m+h=5$ or when $m+h=2$;
n+s can never be greater than 2;
m+h can never be greater than 5;
h=3 and m=1 when R=methyl and q=1 and p=0;
h=2 and m=1 when R=ethyl and q=1 and p=0 or when q=0 and p=1;
h=1 and m=3 when p=1 and q=0;
r and t=0 when $n+s=3$ or when $n+s=0$;
s=0 when n, r and t=1 or when n=2, r=0 and t=1;
s=1 when n=1 and t and r=0 or 1 but only one of t and r can be 1;
s=2 when t=1 and n=0;
$m+h=5$ or 4, when p and q=0;
m and q=1 and p=0 when h=3, 2 or 1 but R can only be ethyl when h=1, 2 and R can only be methyl when h=2, 3;
h+m can never be greater than 5;
n+s can never be greater than 2;
q=0 and p=1 and h=2 when m=1 or 0;
q=0 and p=1 and 1=1 when m=3 or 2;

r and t=0 when $n+s=3$ or when n=0 and s=2;
t=1 when n=0 or 1 and s=1 or 2;
n and t=1 when s=0 and r=1.

10. A mixture of isomerice enals in accord with claim 1 and further characterized as having most of the aldehydes in the mixture represented by the structure set forth below, and their saturated aldehyde, alcohol, ethoxylated alcohol, and ethoxylated alcohol sulfate derivatives:

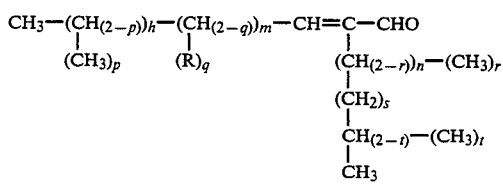

Wherein:
R=methyl or ethyl; h and m=0, 1, 2, 3, 4 and 5;
n and s=0, 1, 2; p, q, r and t=—0, 1;
$m+h=5$ or 4, when p and q=0;
m and q=1 and p=0 when h=3, 2 or 1 but R can only be ethyl when h=1, 2 and R can only be methyl when h=2, 3;
h+m can never be greater than 5;
n+s can never be greater than 2;
q=0 and p=1 and h=2 when m=1 or 0;
q=0 and p=1 and h=1 when m=3 or 2;
r and t=0 when $n+s=3$ or when n=0 and s=2;
t=1 when n=0 or 1 and s=1 or 2;
n and t=1 when s=0 and r=1.

11. The enals of claim 4 in which about 40 to 60% by weight of the enals are 2(3-methylbutyl)-5-methyl-2-octenal, 2(1-methylbutyl)-5-methyl-2-octenal and 2-pentyl-5-methyl-2-octenal.

12. As a new compound, a $C_{14}$ enal suitable for conversion to compounds for use in detergents, and in liquid form, designated as 2(3-methylbutyl)-5-methyl-2-octenal.

13. As a new compound a $C_{14}$ enal suitable for conversion to compounds for use in detergents, and in liquid form, designated as 2(1-methylbutyl)-5-methyl-2-octenal.

* * * * *